United States Patent
Ehmke

(10) Patent No.: US 10,080,596 B2
(45) Date of Patent: Sep. 25, 2018

(54) HIP FIXATION WITH LOAD-CONTROLLED DYNAMIZATION

(71) Applicant: Acumed LLC, Hillsboro, OR (US)

(72) Inventor: Larry W. Ehmke, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 0 days.

(21) Appl. No.: 15/216,646

(22) Filed: Jul. 21, 2016

(65) Prior Publication Data

US 2017/0014167 A1    Jan. 19, 2017

Related U.S. Application Data

(63) Continuation-in-part of application No. 14/565,105, filed on Dec. 9, 2014, now Pat. No. 9,463,055, and a
(Continued)

(51) Int. Cl.
*A61B 17/70* (2006.01)
*A61B 17/72* (2006.01)
(Continued)

(52) U.S. Cl.
CPC .......... *A61B 17/725* (2013.01); *A61B 17/746* (2013.01); *A61B 17/748* (2013.01);
(Continued)

(58) Field of Classification Search
None
See application file for complete search history.

(56) References Cited

U.S. PATENT DOCUMENTS

| | | | |
|---|---|---|---|
| 2,699,774 A | 1/1955 | Livingston | |
| 4,129,903 A | 12/1978 | Huggler | |

(Continued)

FOREIGN PATENT DOCUMENTS

| | | |
|---|---|---|
| EP | 1797835 A1 | 6/2007 |
| FR | 2686788 A1 | 8/1993 |
| JP | 4017211 B2 | 9/2007 |
| WO | 2008022136 A2 | 2/2008 |
| WO | 2008098728 A2 | 8/2008 |
| WO | 2013075730 A1 | 5/2013 |

OTHER PUBLICATIONS

Biomet Trauma, "VHS® Vari-Angle Hip System Surgical Technique" brochure, (c) 2008 Biomet, rev. Mar. 2008, 12 pages.
(Continued)

*Primary Examiner* — Eduardo C Robert
*Assistant Examiner* — Tara R Carter
(74) *Attorney, Agent, or Firm* — Kolisch Hartwell, P.C.

(57) ABSTRACT

System, including methods and apparatus, for hip fixation with load-controlled dynamization. In exemplary embodiments, the system may comprise a fixation element, such as a screw, configured to be placed into a proximal femur of a subject, with a leading end of the fixation element anchored in a head of the proximal femur. The system also may comprise a stop member configured to be connected (e.g., via a nail or plate) to the proximal femur. The system further may comprise a deformable member configured to be irreversibly deformed by compressive force exerted on at least a portion of the deformable member by the fixation element and the stop member in response to a load applied to the proximal femur by the subject, such that the fixation element and the stop member move relative to one another parallel to a long axis of the fixation element.

20 Claims, 8 Drawing Sheets

Related U.S. Application Data continuation-in-part of application No. 14/565,116, filed on Dec. 9, 2014, now Pat. No. 9,433,448, and a continuation-in-part of application No. 14/566,350, filed on Dec. 10, 2014, now Pat. No. 9,433,451, and a continuation-in-part of application No. 14/706,922, filed on May 7, 2015, now Pat. No. 9,526,542, said application No. 14/566,350 is a continuation-in-part of application No. 14/565,105, filed on Dec. 9, 2014, now Pat. No. 9,463,055, and a continuation-in-part of application No. 14/565,116, filed on Dec. 9, 2014, now Pat. No. 9,433,448.

(60) Provisional application No. 61/913,593, filed on Dec. 9, 2013, provisional application No. 61/913,611, filed on Dec. 9, 2013, provisional application No. 61/914,180, filed on Dec. 10, 2013, provisional application No. 61/989,662, filed on May 7, 2014.

(51) Int. Cl.
 A61B 17/80 (2006.01)
 A61B 17/86 (2006.01)
 A61B 17/74 (2006.01)

(52) U.S. Cl.
 CPC ...... A61B 17/8038 (2013.01); A61B 17/8061 (2013.01); A61B 17/863 (2013.01)

(56) References Cited

U.S. PATENT DOCUMENTS

| | | |
|---|---|---|
| 4,399,813 A | 8/1983 | Barber |
| 4,657,001 A | 4/1987 | Fixel |
| 4,776,330 A | 10/1988 | Chapman et al. |
| 4,959,064 A | 9/1990 | Engelhardt |
| 5,032,125 A | 7/1991 | Durham et al. |
| 5,041,116 A | 8/1991 | Wilson |
| 5,098,434 A | 3/1992 | Serbousek |
| 5,176,681 A | 1/1993 | Lawes et al. |
| 5,578,035 A | 11/1996 | Lin |
| 5,728,099 A | 3/1998 | Tellman et al. |
| 5,743,912 A | 4/1998 | Lahille et al. |
| 5,759,184 A | 6/1998 | Santangelo |
| 6,102,951 A | 8/2000 | Sutter et al. |
| 6,106,528 A | 8/2000 | Durham et al. |
| 6,238,126 B1 | 5/2001 | Dall |
| 6,296,645 B1 | 10/2001 | Hover et al. |
| 6,443,954 B1 | 9/2002 | Bramlet et al. |
| 6,468,278 B1 | 10/2002 | Mückter |
| 6,562,042 B2 | 5/2003 | Nelson |
| 6,645,209 B2 | 11/2003 | Hall, IV et al. |
| 6,648,889 B2 | 11/2003 | Bramlet et al. |
| 6,695,844 B2 | 2/2004 | Bramlet et al. |
| 6,783,530 B1 | 8/2004 | Levy |
| 6,855,146 B2 | 2/2005 | Frigg et al. |
| 7,041,104 B1 | 5/2006 | Cole et al. |
| 7,135,023 B2 | 11/2006 | Watkins et al. |
| 7,175,626 B2 | 2/2007 | Neff |
| 7,503,919 B2 | 3/2009 | Shaw |
| 7,569,055 B2 | 8/2009 | Zander et al. |
| 7,591,819 B2 | 9/2009 | Zander et al. |
| 7,763,023 B2 | 7/2010 | Gotfried |
| 7,972,336 B2 | 7/2011 | James et al. |
| 8,114,078 B2 | 2/2012 | Aschmann |
| 8,137,348 B2 | 3/2012 | Gotfried |
| 8,157,803 B1 | 4/2012 | Zirkle, Jr. et al. |
| 8,158,802 B2 | 4/2012 | Lahm et al. |
| 8,172,841 B2 | 5/2012 | Défossez |
| 8,177,786 B2 | 5/2012 | Leyden et al. |
| 8,241,287 B2 | 8/2012 | Prager et al. |
| 8,252,059 B2 | 8/2012 | Overes et al. |
| 8,287,540 B2 | 10/2012 | LeCronier et al. |
| 8,398,636 B2 | 3/2013 | Simon et al. |
| 8,414,582 B2 | 4/2013 | Overes et al. |
| 8,617,227 B2 | 12/2013 | Sucec et al. |
| 8,790,343 B2 | 7/2014 | McClellan et al. |
| 9,254,153 B2 | 2/2016 | Simon et al. |
| 9,526,542 B2 | 12/2016 | Ehmke |
| 2002/0007185 A1 | 1/2002 | Aghion |
| 2002/0032445 A1 | 3/2002 | Fujiwara |
| 2002/0173792 A1 | 11/2002 | Severns et al. |
| 2003/0074000 A1 | 4/2003 | Roth et al. |
| 2004/0260290 A1 | 12/2004 | Zander et al. |
| 2005/0010224 A1 | 1/2005 | Watkins et al. |
| 2005/0055024 A1 | 3/2005 | James et al. |
| 2005/0143739 A1 | 6/2005 | Shinjo et al. |
| 2005/0203510 A1 | 9/2005 | Sohngen |
| 2006/0069392 A1 | 3/2006 | Renzi Brivio et al. |
| 2006/0084999 A1 | 4/2006 | Aschmann |
| 2006/0095039 A1 | 5/2006 | Mutchler |
| 2006/0149248 A1 | 7/2006 | Schlienger et al. |
| 2006/0155281 A1 | 7/2006 | Kaup et al. |
| 2006/0200160 A1 | 9/2006 | Border et al. |
| 2006/0241604 A1 | 10/2006 | Frigg et al. |
| 2006/0241606 A1 | 10/2006 | Vachtenberg et al. |
| 2007/0100343 A1 | 5/2007 | Cole et al. |
| 2007/0219636 A1 | 9/2007 | Thakkar |
| 2007/0233103 A1 | 10/2007 | Metzinger |
| 2007/0270847 A1 | 11/2007 | Shaw |
| 2008/0140077 A1 | 6/2008 | Kebaish |
| 2008/0147127 A1* | 6/2008 | Tipirneni ............ A61B 17/742 606/301 |
| 2008/0177291 A1 | 7/2008 | Jensen et al. |
| 2008/0183170 A1 | 7/2008 | Metzinger et al. |
| 2008/0255559 A1 | 10/2008 | Leyden et al. |
| 2008/0269752 A1 | 10/2008 | Simon et al. |
| 2008/0269807 A1* | 10/2008 | Simon ................. A61B 17/746 606/290 |
| 2008/0281326 A1 | 11/2008 | Watanabe et al. |
| 2009/0048600 A1 | 2/2009 | Matityahu et al. |
| 2009/0048606 A1 | 2/2009 | Tipirneni et al. |
| 2009/0088752 A1 | 4/2009 | Metzinger et al. |
| 2009/0248025 A1 | 10/2009 | Haidukewych et al. |
| 2009/0326534 A1 | 12/2009 | Yamazaki et al. |
| 2010/0121327 A1 | 5/2010 | Velikov |
| 2010/0179549 A1 | 7/2010 | Keller et al. |
| 2010/0179551 A1 | 7/2010 | Keller et al. |
| 2010/0249781 A1 | 9/2010 | Haidukewych et al. |
| 2010/0249852 A1 | 9/2010 | Brumfield et al. |
| 2010/0268285 A1 | 10/2010 | Tipirneni et al. |
| 2010/0312245 A1 | 12/2010 | Tipirneni et al. |
| 2010/0331843 A1 | 12/2010 | Grusin |
| 2011/0196370 A1 | 8/2011 | Mikhail |
| 2011/0295255 A1 | 12/2011 | Roberts et al. |
| 2012/0109128 A1 | 5/2012 | Frigg |
| 2012/0130370 A1 | 5/2012 | Kinmon |
| 2012/0136356 A1 | 5/2012 | Doherty et al. |
| 2012/0310289 A1 | 12/2012 | Bottlang et al. |
| 2013/0041414 A1 | 2/2013 | Epperly et al. |
| 2013/0204304 A1 | 8/2013 | Bottlang et al. |
| 2014/0052132 A1 | 2/2014 | Matityahu et al. |
| 2014/0058392 A1 | 2/2014 | Mueckter et al. |
| 2014/0094802 A1 | 4/2014 | Simon et al. |
| 2014/0135769 A1 | 5/2014 | Ziran |
| 2014/0214035 A1 | 7/2014 | Simon |
| 2014/0214098 A1 | 7/2014 | Probe et al. |
| 2014/0330274 A1 | 11/2014 | Matityahu et al. |
| 2015/0157368 A1 | 6/2015 | Ehmke et al. |
| 2015/0157369 A1 | 6/2015 | Ehmke et al. |
| 2015/0157371 A1 | 6/2015 | Ehmke et al. |
| 2015/0250507 A1 | 9/2015 | Harrison et al. |
| 2016/0051295 A1 | 2/2016 | Nakumura et al. |

OTHER PUBLICATIONS

Copenheaver, Blaine, Authorized Officer, International Searching Authority, U.S. Patent and Trademark Office, "International Search Report" in connection with related International Application No. PCT/US2015/029789, dated Aug. 7, 2015, 2 pages.

Copenheaver, Blaine, Authorized Officer, International Searching Authority, U.S. Patent and Trademark Office, "Written Opinion of

(56) References Cited

OTHER PUBLICATIONS the International Searching Authority" in connection with related International Application No. PCT/US2015/029789, dated Aug. 7, 2015, 9 pages.

Leung, Kwok Sui et al., "Gamma3 Trochanteric Nail 180 Operative Technique" brochure, Stryker Trauma GmbH, (c) 2011, 52 pages.

Matityahu, Amir et al., "The Variable Angle Hip Fracture Nail Relative to the Gamma 3: A Finite Element Analysis Illustrating the Same Stiffness and Fatigue Characteristics", Hindawi Publishing Corporation, Advances in Orthopedics, vol. 213, Article ID 143801, (c) 2013, 12 pages.

European Patent Office, "Extended European Search Report" in connection with related European Patent App. No. 15789941.0, dated Feb. 20, 2018, 11 pgs.

* cited by examiner

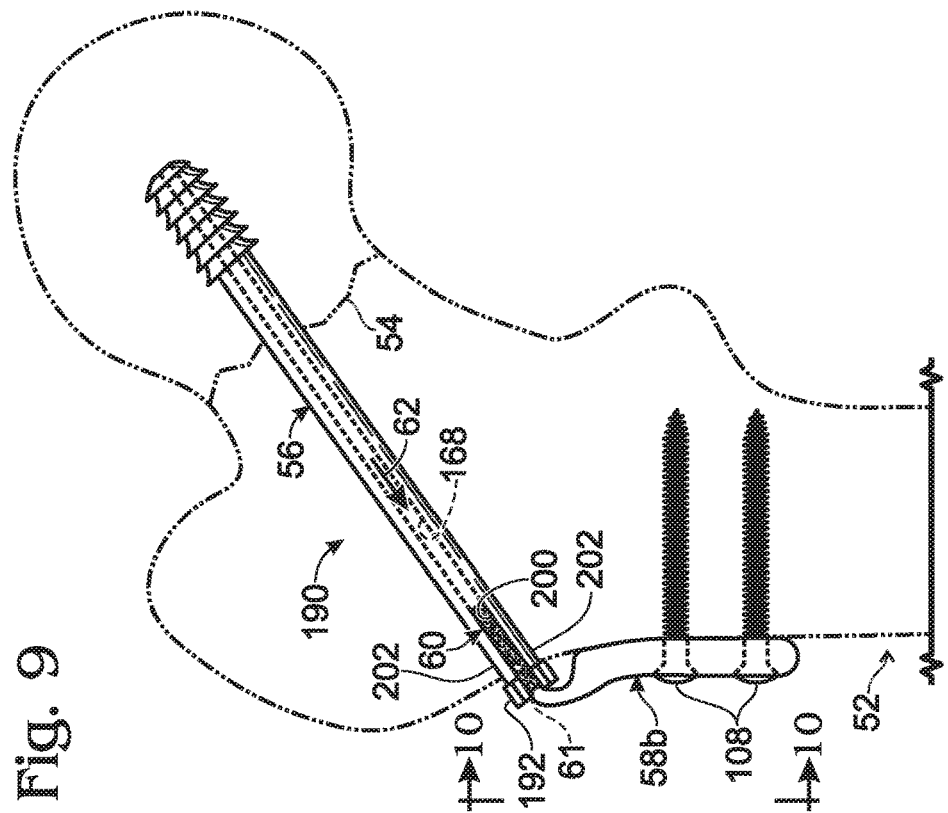
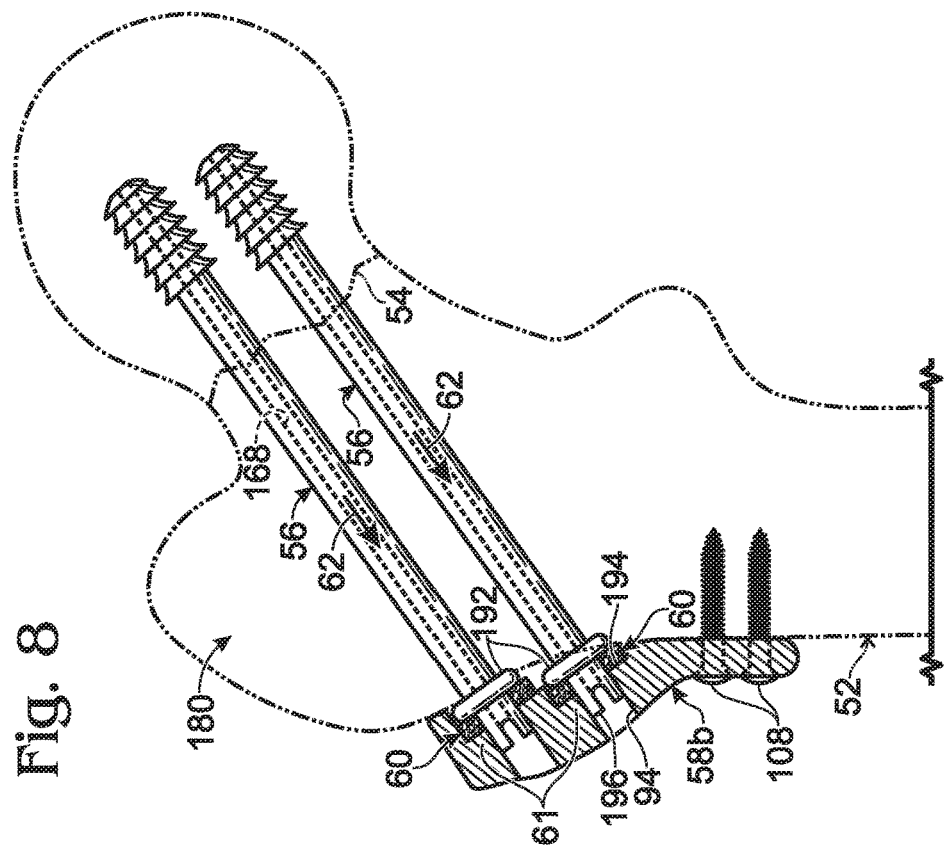

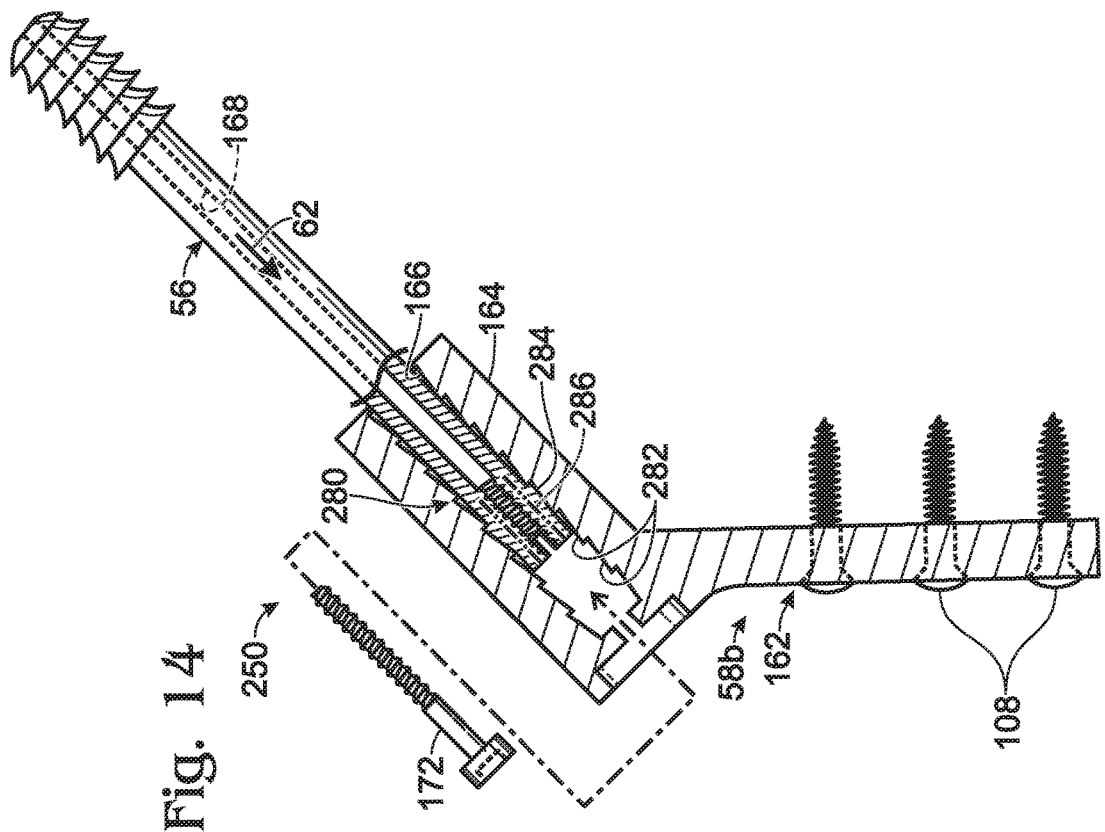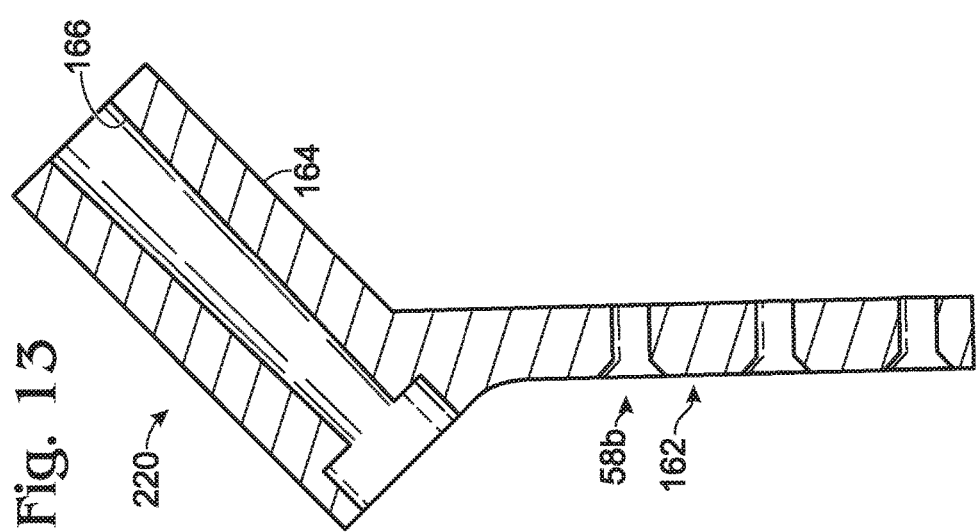

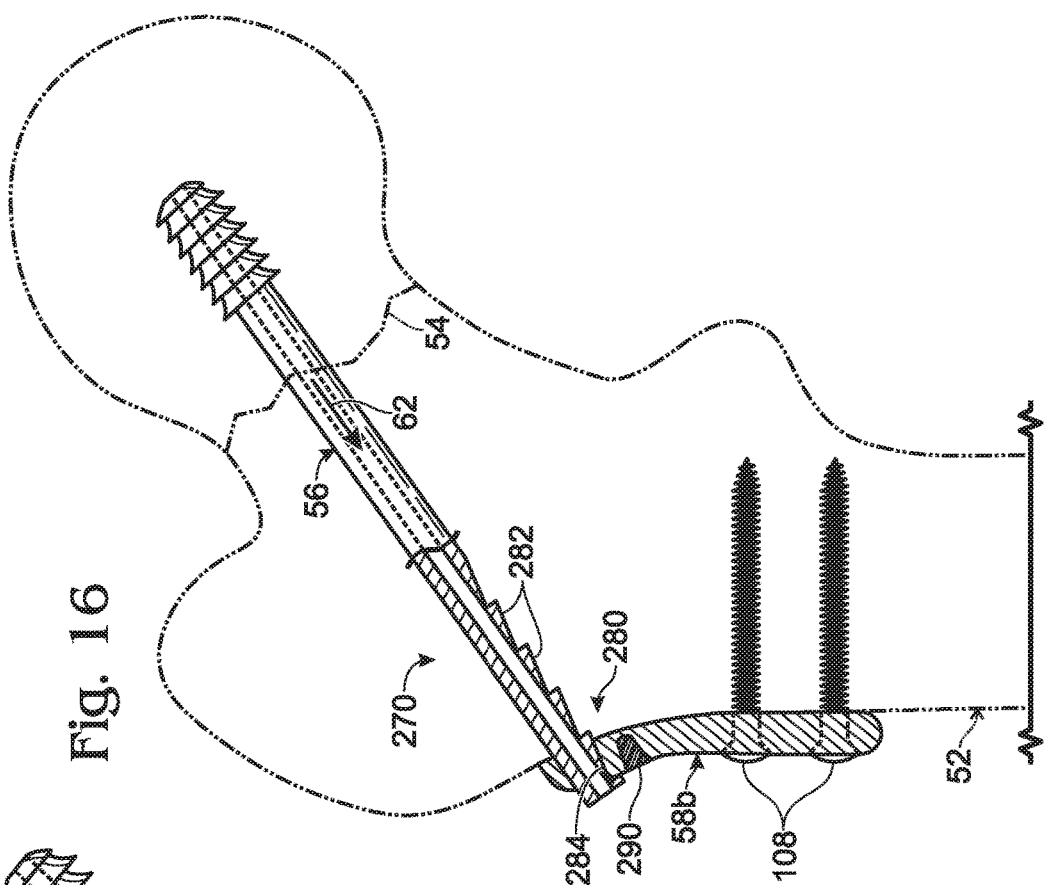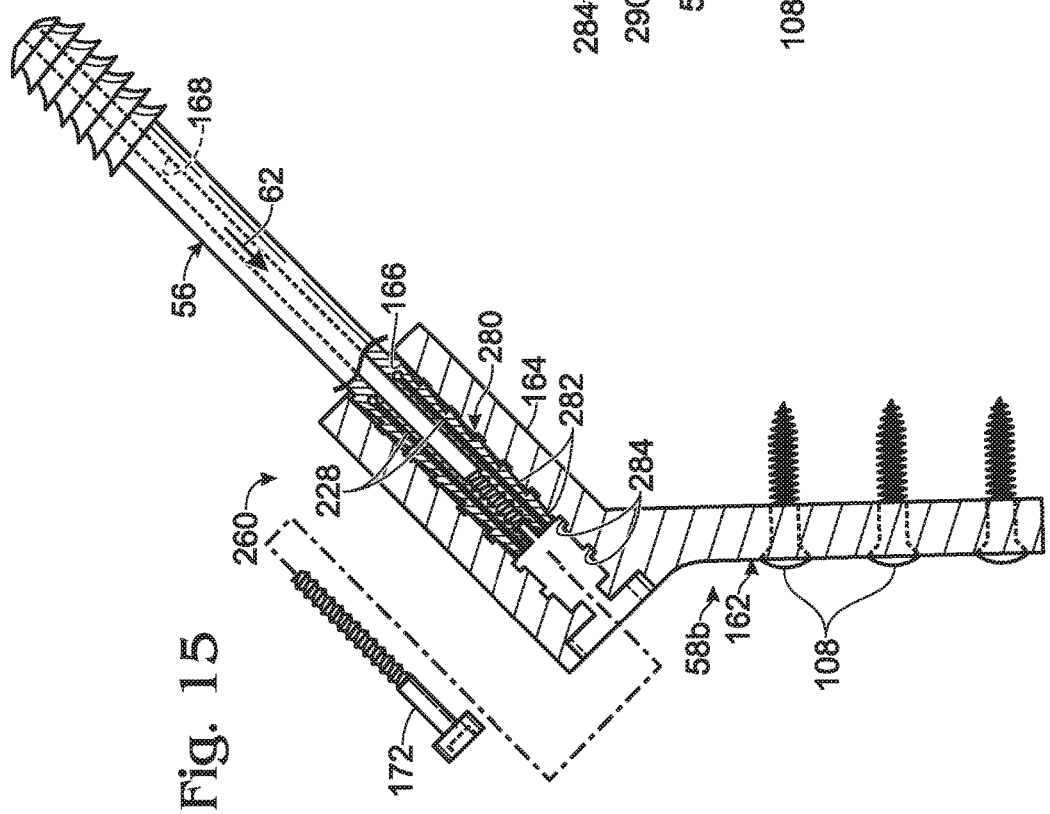

HIP FIXATION WITH LOAD-CONTROLLED DYNAMIZATION

CROSS-REFERENCES TO PRIORITY APPLICATIONS

This application is a continuation-in-part of the following U.S. patent applications: U.S. patent application Ser. No. 14/565,105, filed Dec. 9, 2014; U.S. patent application Ser. No. 14/565,116, filed Dec. 9, 2014; U.S. patent application Ser. No. 14/566,350, filed Dec. 10, 2014; and U.S. patent application Ser. No. 14/706,922, filed May 7, 2015.

U.S. patent application Ser. No. 14/565,105, in turn, is based upon and claims the benefit under 35 U.S.C. § 119(e) of U.S. Provisional Patent Application Ser. No. 61/913,593, filed Dec. 9, 2013.

U.S. patent application Ser. No. 14/565,116, in turn, is based upon and claims the benefit under 35 U.S.C. § 119(e) of U.S. Provisional Patent Application Ser. No. 61/913,611, filed Dec. 9, 2013.

U.S. patent application Ser. No. 14/566,350, in turn, is a continuation-in-part of U.S. patent application Ser. No. 14/565,105 and U.S. patent application Ser. No. 14/565,116, with priority claims as listed above, and is based upon and claims the benefit under 35 U.S.C. § 119(e) of U.S. Provisional Patent Application Ser. No. 61/914,180, filed Dec. 10, 2013.

U.S. patent application Ser. No. 14/706,922, in turn, is based upon and claims the benefit under 35 U.S.C. § 119(e) of U.S. Provisional Patent Application Ser. No. 61/989,662, filed May 7, 2014.

Each of these priority patent applications is incorporated herein by reference in its entirety for all purposes.

INTRODUCTION

The hip joint is a synovial joint formed by articulation of the head of the femur (the femoral head) with the acetabulum of the pelvis. The hip joint(s) supports the weight of the body when a person is standing, walking, or running, among others.

Trauma to the femur can fracture the femur near the hip joint. Depending on the position and severity of fracture, the femoral head may be replaced with a prosthesis, or the femur may be stabilized with an implanted fixation system to stabilize the femoral head while the femur heals. The fixation system may include a plate or a nail, among others.

Components of the fixation system may be freely slidable or fixed rigidly relative to one another, to respectively allow or prevent intra-femoral movement at the fracture site. However, neither approach may be optimal. An improved hip fixation system is needed.

SUMMARY

The present disclosure provides a system, including methods and apparatus, for hip fixation with load-controlled dynamization. In exemplary embodiments, the system may comprise a fixation element, such as a screw, configured to be placed into a proximal femur of a subject, with a leading end of the fixation element anchored in a head of the proximal femur. The system also may comprise a stop member configured to be connected (e.g., via a nail or plate) to the proximal femur. The system further may comprise a deformable member configured to be irreversibly deformed by compressive force exerted on at least a portion of the deformable member by the fixation element and the stop member in response to a load applied to the proximal femur by the subject, such that the fixation element and the stop member move relative to one another parallel to a long axis of the fixation element.

BRIEF DESCRIPTION OF THE DRAWINGS

FIG. 8 is a partially sectional view of still another exemplary embodiment of a hip fixation system with load-controlled dynamization via plastic deformation of a deformable member of the system, with the system attached to a fractured femur and including a plurality of deformable spacer elements each capable of plastic deformation in response to a load applied to the system, in accordance with aspects of the present disclosure.

FIG. 9 is a front view of still yet another exemplary embodiment of a hip fixation system with load-controlled dynamization via plastic deformation of a deformable member of the system, with the system attached to a fractured femur and including a support member mounted to the lateral cortex of the femur and also including a fixation element anchored in the femoral head and attached to a deformable member that is deformed by contact with a stop member of the support member, in accordance with aspects of the present disclosure.

FIG. 13 is a somewhat schematic sectional view of the side plate of FIG. 12, taken as in FIG. 12 but with the internal taper of the barrel portion exaggerated.

FIG. 14 is a partially sectional and exploded view of an exemplary embodiment of a hip fixation system having load-controlled dynamization governed by a ratchet, in accordance with aspects of the present disclosure.

FIG. 15 is a partially sectional and exploded view of another exemplary embodiment of a hip fixation system having load-controlled dynamization governed by a ratchet, in accordance with aspects of the present disclosure.

FIG. 16 is a partially sectional view of a yet another exemplary embodiment of a hip fixation system having load-controlled dynamization governed by a ratchet, in accordance with aspects of the present disclosure.

DETAILED DESCRIPTION

Figure 1:
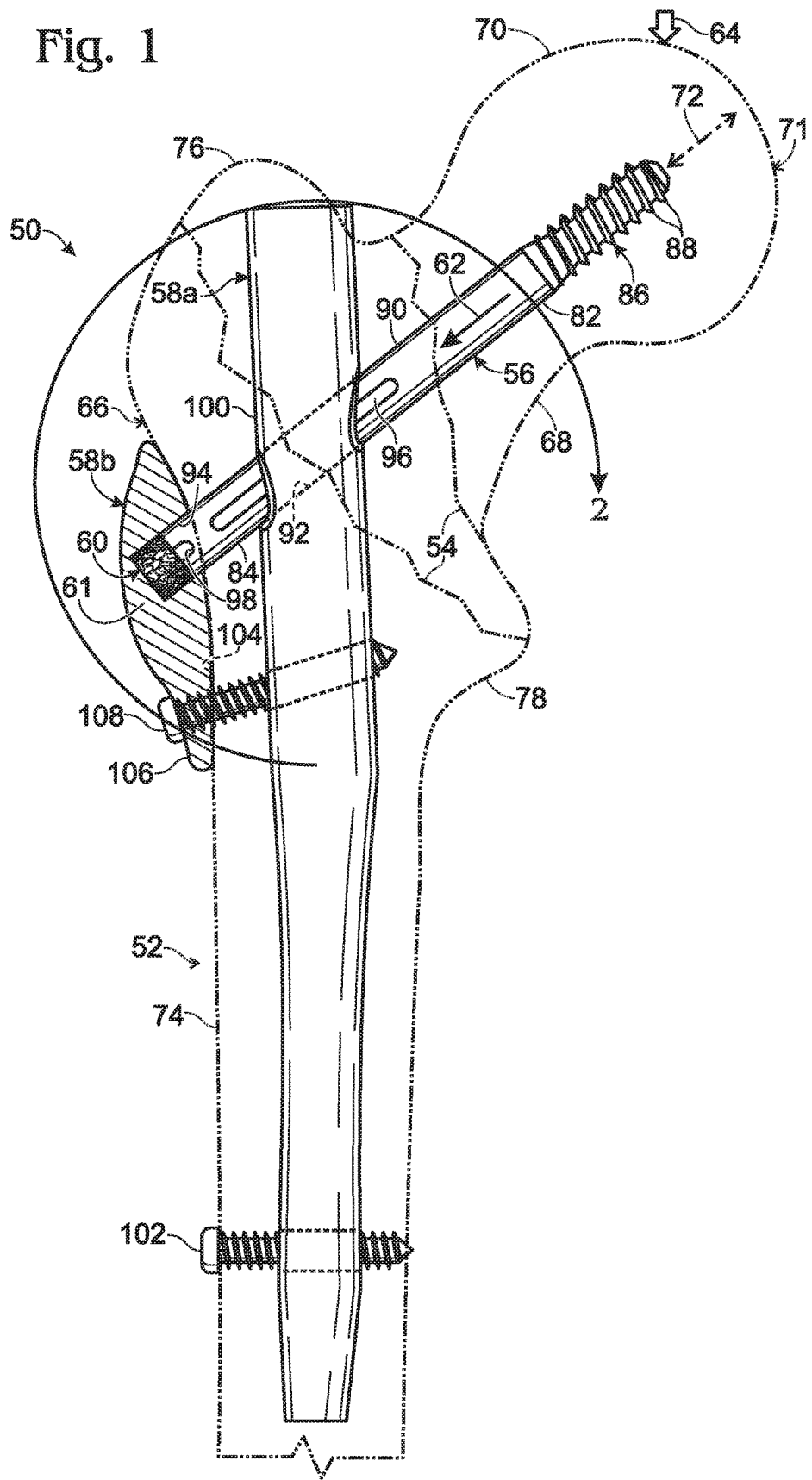
FIG. 1 is a front, partially sectional view of selected aspects of an exemplary hip fixation system installed in a fractured femur of a subject and configured for load-controlled dynamization through deformation of a deformable region of the system, in accordance with aspects of the present disclosure.

The present disclosure provides a system, including methods and apparatus, for hip fixation with load-controlled dynamization. In exemplary embodiments, the system may comprise a fixation element, such as a screw, configured to be placed into a proximal femur of a subject, with a leading end of the fixation element anchored in a head of the proximal femur. The system also may comprise a stop member configured to be connected (e.g., via a nail or plate) to the proximal femur. The system further may comprise a deformable member configured to be irreversibly deformed by compressive force exerted on at least a portion of the deformable member by the fixation element and the stop member in response to a load applied to the proximal femur by the subject, such that the fixation element and the stop member move relative to one another parallel to a long axis of the fixation element.

The load-controlled dynamization disclosed herein may have various advantages over other hip fixation systems. The ability of system components to move relative to one another in a load-controlled manner reduces the incidence of cutout of the fixation element through the femoral head, relative to a system in which system components are rigidly attached to one another. Controlling and limiting movement of system components reduces femoral shortening and establishes a limit for the amount of femoral shortening that can occur, relative to a system where system components are freely slidable relative to one another.

Further aspects of the present disclosure are described in the following sections: (I) overview of an exemplary hip fixation system, (II) methods of hip fixation, (III) composition of system components, (IV) kits, and (V) examples.

I. OVERVIEW OF AN EXEMPLARY HIP FIXATION SYSTEM

This section provides an overview of an exemplary hip fixation system configured for load-controlled dynamization through deformation of a deformable region of the system; see FIGS. 1-5.

Load-controlled dynamization may permit post-surgical compression of a femoral fracture to accommodate settling of the fracture (e.g., shortening of the femoral neck). "Load-controlled dynamization," as used herein, is any movement and/or change in position of portions of the hip fixation system relative to one another that is caused by a load applied to the hip fixation system and/or the femur, typically by a subject into which the system has been installed. The dynamization may be "distance-limited," which means that additional movement within the fixation system requires increasing force according to the degree of movement and/or change in position that the fixation system has already undergone, optionally with a maximum distance of dynamization predefined for the system. Load-controlled dynamization of the hip fixation system generally results in a corresponding load-controlled dynamization of portions of the femur relative to each other, such as dynamization of the femoral head (a medial portion of the femur) and the femoral body/shaft (a lateral portion of the femur) relative to one another.

FIG. 1 shows a front view of selected aspects of a hip fixation system 50 attached to a femur 52 having at least one discontinuity, such as a fracture 54 or a cut. Fracture 54 may include an intracapsular fracture (e.g., a neck fracture) and/or an extracapsular fracture (e.g., an intertrochanteric fracture).

System 50 may include at least one fixation element 56 (e.g., one, two, three, or more fixation elements), one or more support members 58a, 58b operatively associated with the fixation element, a deformable member 60, and a stop member 61. The deformable member may be capable of deformation that allows the fixation element and the stop member (and/or support member(s)) to move relative to one another, indicated by a motion arrow at 62, such that the femur is compressed at fracture 54. The deformation may occur after the system is installed in a subject, in response to a load 64 applied by the subject to the system and/or femur 52. The amount of deformation that occurs may vary with the applied load, within a load range that causes deformation. The deformable member may undergo plastic (irreversible) deformation and/or elastic (reversible) deformation as the fixation element and the stop member/support member(s) move relative to one another. Furthermore, the resistance to further movement may increase according to the extent to which the deformable member has already been deformed, such that an increasing load is required for progressive movement of the system components relative to one another. In some embodiments, the deformable member may be omitted.

Fixation element 56 may change in length and/or axial position along its long axis, in response to load 64 (e.g., a downward force) applied to the fixation element via femur 52. The load may be applied by a recipient of the fixation system, also called a subject, generally using at least a portion of the subject's weight. In other words, the load may be applied post-surgery, such as when the subject stands, walks, or runs, among others. The maximum load applied by the subject to fixation element 56 may determine the magnitude of the change in length and/or axial position of the fixation element, optionally up to a load limit and/or within a load range (such as a predefined/particular load range). The change in length and/or axial position may be accompanied by motion of the femoral head and the femoral shaft relative to one another, which may apply compression to fracture 54 (or other discontinuity).

Fixation element 56 interchangeably may be termed a transverse member, a femoral head fastener, or a femoral head anchor. The fixation element may be configured to be implanted transversely to a long axis of femur 52. The fixation element extends from a lateral portion 66 (also called a body) of femur 52, through a femoral neck 68, and into a femoral head 70 (forming a medial portion 71 of the femur). The fixation element may be anchored to medial portion 71 and slidable with respect to lateral portion 66 of the femur. A long axis 72 defined by fixation element 56 (and/or a shaft thereof) may have any suitable transverse orientation with respect to the long axis of femur 52, such as forming an angle of at least about 100 degrees, less than about 150 degrees, or a combination thereof, among others. In exemplary embodiments, the fixation element is oriented at about 120 to 145 degrees with respect to the femoral long axis. Lateral portion 66 of the femur includes a shaft 74 of the femur and may include at least part of greater trochanter 76 and/or lesser trochanter 78.

Fixation element 56 may impose any suitable restrictions on intra-femoral motion. For example, the fixation element may restrict rotational motion of the femoral head relative to the femoral shaft, such as varus motion of the femoral head. Also, the fixation element may permit limited motion of the femoral head relative to the femoral shaft in a direction parallel to long axis 72.

The fixation element may have a leading portion 82 (interchangeably termed a spanning portion) disposed in femoral head 70, and a trailing portion 84 disposed at least partially in lateral portion 66 of the femur. (The leading portion enters bone before the trailing portion during installation.) One or both portions 82, 84 of the fixation element may be anchored in the femur. More particularly, one or both portions 82, 84 may include an anchoring structure 86, such as an external thread 88, that engages bone to restrict movement of the fixation element with respect to bone in both directions parallel to long axis 72. Accordingly, the fixation element may be a screw, such as a lag screw, with a thread only on leading portion 82. The anchoring structure may be formed integrally with a shaft 90 of the fixation element or may be provided by a discrete component that is movable relative to the shaft. Exemplary anchoring structures include an external thread, one or more barbs, one or more flanges (e.g., annular or helical flanges), at least one extendable pin (e.g., a talon), a pivotably deployed retainer, or any combination thereof, among others. In some embodiments, trailing portion 84 of fixation element 56 does not include an anchoring structure. The fixation element may be cannulated, with a bore extending axially through the leading portion, the trailing portion, or both (e.g., through the entire length of the fixation element.) In some embodiments, the fixation element may have a head near or at the trailing end of the fixation element (e.g., see Example 3).

Fixation element 56 may be disposed completely in the femur or may project from the femur, such as projecting from a lateral side of the femur as shown in FIG. 1. Generally, only a fraction, if any, of the fixation element projects from the femur, such as less than 10% or 5% by length, among others.

The fixation element may extend into and/or through at least one support member 58a or 58b. For example, in the depicted embodiment, the fixation element extends through an opening 92 defined by inner support member 58a and into an opening 94 defined by outer support member 58b. Each opening 92, 94 may be a blind hole or a through-hole, among others. The fixation element may be slidably disposed with respect to at least one support member (and/or stop member 61) to permit motion parallel to long axis 72 as deformable member 60 deforms.

Fixation element 56 may be formed as only one piece or may be formed by an assembly of two or more discrete components/pieces that are placed into the femur as a unit. In some embodiments, the fixation element may be attachable to a compression screw via a trailing portion of the fixation element, after the fixation element has been placed into the femur. The compression screw may be turned to adjust a compression applied to the femur at a fracture 54 (e.g., see Examples 2, 4, and 5). The compression screw may extend through an opening defined by deformable member 60.

The fixation element may have any suitable shape. For example, the fixation element may have a circular cross section and/or may include a cylindrical shaft. In some embodiments, the shaft may include opposing ends and a lateral surface extending between the opposing ends. The lateral surface may include at least one non-cylindrical region. The non-cylindrical region may be a flat region, such as one or more longitudinal flats, or at least one trough 96, among others (e.g., see Example 1). Deformable member 60 may or may not be attached to the shaft, such that the fixation element and the deformable member can be placed into the femur as a unit. If attached, the deformable member may be attached to a non-cylindrical surface region of the shaft.

The fixation element may have a driver engagement structure 98 to allow the element to interface with a driver for advancement into bone. In the depicted embodiment, driver engagement structure 98 is a transverse notch formed at the trailing end of the element. In other embodiments, the driver engagement structure may include external facets or a socket (e.g., a hex socket), among others.

Each of support members 58a, 58b may be operatively associated with fixation element 56 by installation into the femur. A pair of members/components of a system that are "operatively associated" are positioned to allow direct contact with one another, or are separated by one or more intervening, implanted members/components of the system that collectively extend from one member/component of the pair to the other member/component of the pair. Each support member 58a, 58b (and/or stop member 61) may have a fixed position with respect to lateral portion 66 of the femur after installation.

Inner support member 58a may be a nail 100 (interchangeably termed an intramedullary nail) disposed at least predominantly inside the femur. Nail 100 may extend longitudinally in the femur. The nail may be used without outer support member 58b, and outer support member 58b may be used without the nail, or they may be used in combination as shown. The nail may be attached to bone with one or more fasteners 102 that extend into and/or through transverse openings of the nail. At least one fracture 54 or other discontinuity of the femur may be spanned by the nail.

The nail may have any suitable structure. Nail 100 may be linear or nonlinear (e.g., with a longitudinal bend of less than about 10 degrees). The nail may have a leading end region that is smaller in diameter than a trailing end region thereof. The nail may or may not be cannulated longitudinally.

Outer support member 58b may be disposed at least partially outside the femur, such as located on and/or attached to a lateral cortex 104 (interchangeably termed a lateral side) of the femur. The outer support member may include a mounting portion 106 provided by a plate device (which may be a buttress plate or a side plate, among others). The mounting portion may define openings to receive one or more fasteners 108, such as screws, to mount the support member on the femur (and/or to connect support members to one another). Each fastener 108 may or may not extend into nail 100. The outer support member also may or may not include a barrel portion that extends into the femur and receives a trailing portion of fixation element 56 (e.g., see Examples 2, 4, and 5).

Outer support member 58b may include or at least partially contain deformable member 60. The deformable member may or may not be discrete from the fixation element, each support member, and the stop member(s). The deformable member may or may not be attached to the fixation element, a support member, and/or the stop member. Accordingly, in some embodiments, the deformable member may be described as an insert and or may or may not be removable from opening 94 of support member 58b (or opening 92 of support member 58a). Fixation element 56 may extend into opening 94 (or opening 92) to allow the fixation element to apply deforming pressure to deformable member 60, such as to compress the element, with or without direct contact between the fixation element and the deformable member.

Deformable member 60 may have any suitable position relative to fixation element 56, a support member 58a or 58b, and stop member 61. In some embodiments, the deformable member may be operatively disposed between a shaft of the fixation element and the stop member (and/or support member). For example, the deformable member may be attached to a side surface region of the shaft between opposing ends of the shaft, and at least a portion of the deformable member may be disposed between the side surface region and a region of the stop member (e.g., see Example 1). Alternatively, the deformable member may be located between a trailing portion of the shaft and the stop member, and optionally coaxial to the shaft (and/or fixation element) (also see Examples 2 and 3). In some embodiments, the deformable member may be attached to a noncylindrical surface region of the shaft, between opposing ends of the shaft, such as located in a trough defined by the shaft (see Example 1).

Figure 2:
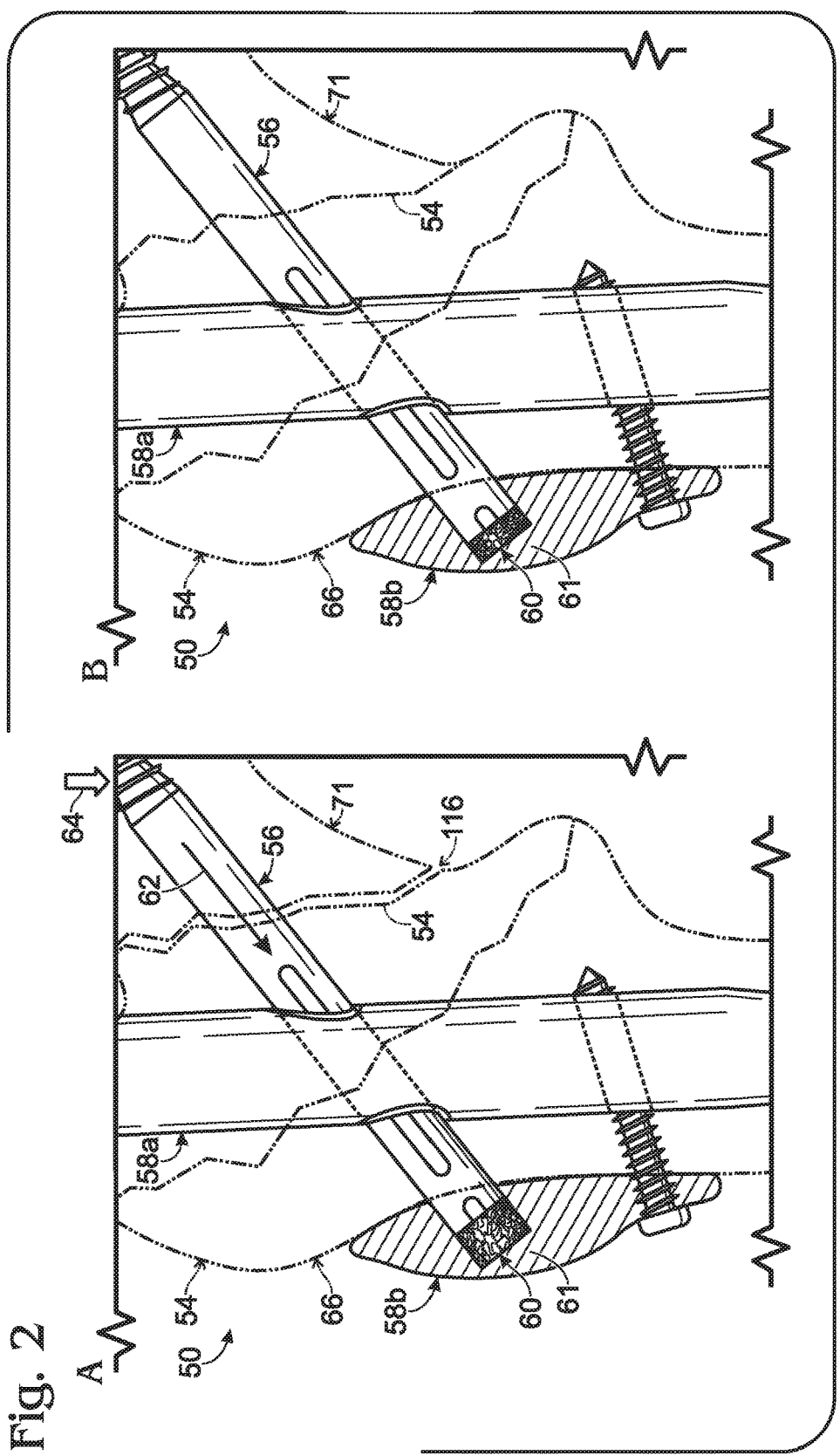
FIG. 2 is a pair of partially sectional, fragmentary views of the fixation system of FIG. 1, taken generally around the region indicated at "2" in FIG. 1 and showing movement of components of the fixation system relative to one another, and associated movement of portions of the femur relative to one another, in response to a deforming load applied to the fixation system by the subject (compare panels A and B), to bring edges of a fracture into contact with one another.

FIG. 2 shows a pair of fragmentary views of fixation system 50 of FIG. 1 taken before (panel A) and after (panel B) permanent compression of at least a portion of deformable member 60. The compression results in movement of fixation element 56 and outer support member 58b (including stop member 61) relative to one another, and movement of lateral and medial portions 66, 71 of the femur relative to one another (e.g., closer to one another). However, to simplify the following discussion, fixation element 56 and medial portion 71 of the femur including the femoral head are considered to be movable, while outer support member 58b, inner support member 58a, stop member 61, and lateral portion 66 of the femur, including the femoral shaft, are considered to be stationary.

Panel A of FIG. 2 shows a gap 116 at fracture 54 between fracture edges of lateral and medial portions 66, 71. Accordingly, load 64 applied to the head of the femur is transmitted efficiently to fixation element 56, instead of being shared between the fixation element and abutted edges of the fracture. As a result, the load produces compression of deformable member 60 in a direction parallel to the long axis of the fixation element. The compression is accompanied by corresponding movement of fixation element 56 and outer support member 58b (including stop member 61) relative to one another, until the gap is closed (compare panels A and B) and the load is shared between the fixation element and the abutted edges of the fracture, or until the load is no longer sufficient to further compress the deformable member. Alternatively, if the fixation element is considered as stationary, outer support member 58b (including stop member 61) (and inner support member 58a) and lateral portion 66 of the femur travel inward, namely, medially and superiorly within the subject, in a direction parallel to the long axis of the fixation element. The fixation element and support member(s)/stop member may be configured to undergo any suitable maximum movement relative to one another, such as at least about 1, 2, or 5 millimeters, and/or up to about 10 millimeters, among others. In other embodiments, relative movement as described above may be permitted and controlled by friction or a ratchet, among others (e.g., see Examples 4 and 5). In some embodiments, movement of the fixation element and the support member(s)/stop member relative to one another may be configured to occur selectively in only one of two opposite axial directions parallel to the long axis of the fixation element and, optionally, without changing the orientation of the fixation element with respect to the support member(s).

In some embodiments, the fixation element may have an integral deformable member that allows the element to undergo a change in length. The length may be reduced by deforming, such as via plastic deformation, a selectively deformable region of the fixation element. The fixation element may undergo any suitable change in length (or axial position), such as at least about 1, 2, or 5 millimeters, and/or up to about 10 millimeters, among others. The deformable region may undergo a corresponding change in dimension.

Deformable member 60 may have any suitable structure and composition. The deformable member may have a plurality of voids that allow the member to be compressed. The deformable member may be formed of metal (such as stainless steel, titanium, etc.), a polymer, or the like. The deformable member may be compressible, which may reduce the volume occupied (e.g., reducing the volume of an imaginary envelope defined by the periphery of the deformable member). The deformable member may be compressible parallel to a first axis without substantially increasing a dimension of the deformable member transverse to the first axis. The deformable member may be irreversibly deformable/compressible (i.e., plastically deformable) or reversibly deformable/compressible (e.g., elastically deformable). Compression of the deformable member may "crush" at least a portion of the deformable region, which is any irreversible compression. The deformable member may include a regular or random array of voids, and may have a cellular and/or porous structure.

The deformable member may be included in and/or at least partially contained by an inner support member, an outer support member, a fixation element, or a stop member, among others. Accordingly, the deformable member may be formed integrally with the support member, fixation element, or stop member, or may be inserted into, attached to, and/or formed on and/or in a support member, fixation element, or stop member.

Figure 3:
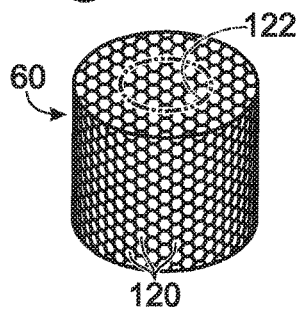
FIG. 3 is a view of an exemplary deformable spacer element to provide a deformable region for any of the hip fixation systems of the present disclosure, with the element having a cellular structure formed by 3-D printing to render the element crushable by plastic deformation to reduce the volume occupied by the element, in accordance with aspects of the present disclosure.

FIG. 3 shows an exemplary deformable member 60 for hip fixation system 50. The deformable member may have a plurality of voids 120, which may give the deformable member a honeycomb-like structure. The deformable member may be formed by, for example, 3-D printing. The deformable member may or may not define an opening 122 (e.g., a through-hole) to receive a portion of the fixation element (such as a shaft region or a head region thereof) and/or a portion of a compression screw that attaches to the fixation element (e.g., see Examples 2 and 3).

Figure 4:
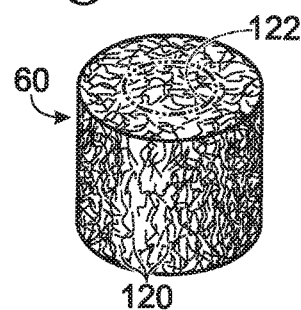
FIG. 4 is a view of another exemplary deformable spacer element to provide a deformable region for any of the hip fixation systems of the present disclosure, with the element being formed by a foam, in accordance with aspects of the present disclosure.

FIG. 4 shows another exemplary deformable member 60 for hip fixation system 50. The deformable member may have a porous structure, such as produced by a foam, for example, a metal foam (e.g., Duocel® foam).

Figure 5:
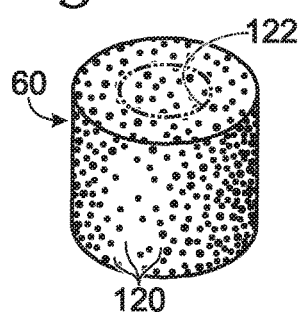
FIG. 5 is a view of still another exemplary deformable spacer element to provide a deformable region for any of the hip fixation systems of the present disclosure, with the element being formed by a polymer, in accordance with aspects of the present disclosure.

FIG. 5 shows still another exemplary deformable member for the hip fixation system of FIG. 1. The deformable member may have a porous structure formed by a polymer or a plasma spray.

In other embodiments, the deformable member may, for example, extend transversely back and forth one or more times (e.g., to create a sinuous structure), follow a helical path, or the like.

Stop member 61 may have any suitable structure and position. The stop member may be formed integrally with a support member (e.g., support member 58b; see FIG. 1 and Example 3) or may be formed separately from the support member and then attached thereto (e.g., see Examples 1 and 2). The stop member may, for example, be attached to the support member by threaded engagement. The stop member may be adjustably positionable parallel to the long axis of the fixation element (e.g., see Example 2) or parallel to the long axis of the support member (e.g., see Example 1), among others. Alternatively, the stop member may be permanently fixed with respect to the support member. The stop member may be positioned coaxially with the fixation element (e.g., see FIG. 1 and Example 2), or may be adjustably offset from the central long axis of the fixation element (see Example 1).

Any of the hip fixation systems of the present disclosure also may include a compliant interface and/or a fixation element 56 that is reversibly flexible (e.g., elastic). The compliant interface (and/or flexible fixation element) may permit off-axis pivotal motion of the fixation element (and/or a region thereof) with respect to a support member (e.g., a nail or a plate) and/or with respect to the shaft of the femur, to reversibly change the orientation of at least a portion of the fixation element. Further aspects of hip fixation systems with a suitable compliant interface and/or flexible fixation element are disclosed in the patent applications listed above under Cross-References, which are incorporated herein by reference.

II. METHODS OF HIP FIXATION

This section describes exemplary methods of hip fixation using any of the fixation systems disclosed herein. The method steps described in this section may be performed in any suitable order and combination and may be combined with any other steps, and performed with any suitable devices and/or combination of device features, disclosed elsewhere herein, such as in Example 6.

A subject's femur to be fixed may be selected. The femur may have at least one discontinuity, such as at least one fracture. The at least one fracture may include an intracapsular fracture and/or an extracapsular fracture. Accordingly, the at least one fracture may include at least one fracture of the femoral body, the femoral neck, and/or the femoral head. The at least one fracture of the femoral body may include an intertrochanteric fracture and/or a subtrochanteric fracture. An intertrochanteric fracture involves the greater trochanter and/or the lesser trochanter and/or is disposed intermediate the trochanters. A subtrochanteric fracture is a fracture that is distal to the lesser trochanter.

A fixation system for fixation of the femur may be selected. The fixation system may include any combination of the elements and features described above in Section I and/or elsewhere in the present disclosure, such as in Section V. The fixation system may include at least one fixation element, one or more support members, at least one stop member, and at least one deformable member. In some embodiments, such as in the case of a femoral neck fracture, a plurality of fixation elements may be selected. A support member may provide a mounting portion for placement on the femur and/or a projecting portion for placement into the femur. The projecting portion may be a barrel portion. In some embodiments, fractures of the femoral neck may be fixed using a support member in the form of a buttress plate having a mounting portion but no projecting portion (e.g., no barrel portion), or without a support member on the femur. In some embodiments, intertrochanteric fractures may be fixed using a plate device having no projecting portion (e.g., no barrel portion), or without a plate device. The plate device may or may not be fastened to the body (e.g., the lateral cortex) of the femur with one or more fasteners (e.g., one or more fasteners that are each distinct from the fixation element).

At least one deformable member may be selected for the fixation system. Each deformable member may be provided by a set of interchangeable deformable members each having a different deformable region. The deformable regions may differ in the deformability of a deformable material that forms each deformable region, in size, in shape, or the like. Selection of a deformable member from the set may be based on at least one characteristic of a recipient of the fixation system, such as the recipient's weight, height, activity level, age, or any combination thereof, among others.

The femur may be stabilized by implanting the fixation system. The fixation element(s) may be placed in the femur, with the fixation element extending from a body to a head of the femur. If a plurality of fixation elements are placed in the femur, they may (or may not) be placed parallel to one another. A plate device may be attached to a lateral surface region of the femur and/or a nail may be placed in a medullary canal of the femur. Each fixation element may extend into (and through) the plate device and/or nail. A deformable member may be operatively disposed in the fixation system. A stop member may be operatively disposed in the fixation system.

A load may be applied to the fixation system via the femur, after the fixation system has been implanted. The load may be applied using the weight of the system recipient.

III. COMPOSITION OF SYSTEM COMPONENTS

Each system component may have any suitable composition. Each may be formed of any suitable biocompatible material(s) and/or bioresorbable (bioabsorbable) material(s). Illustrative biocompatible materials that may be suitable for a fixation element, a plate device, a nail, and/or a deformable member of the fixation system include (1) metal (for example, titanium or titanium alloy, cobalt-chrome alloy, stainless steel, etc.); (2) plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) bioresorbable material or polymer (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.)); (4) bone material or bone-like material (e.g., bone chips, calcium phosphate crystals (e.g., hydroxyapatite, carbonated apatite, etc.)); or (5) any combination thereof.

The system components may be formed of the same or different materials. For example, each may be formed of metal, each may be formed of plastic, or one or more may be formed of metal and another one or more may be formed of plastic, among others.

IV. KITS

The hip fixation system may be provided as a system/kit including at least one fixation element, at least one plate device, at least one nail, one or more fasteners to attach the plate device/nail to bone, at least one deformable member, at least one stop member, or any combination thereof. The system/kit may provide two or more different choices for at least one of the components. For example, the system/kit may include two or more plate devices of different size and/or shape, two or more fixation elements of different size (e.g., different lengths or diameters) and/or compressibility, and/or two or more interchangeable deformable members (e.g., having a different compressibility, a different limit of compressibility, etc.).

V. EXAMPLES

The following examples describe selected aspects and embodiments of the present disclosure including exemplary hip fixation systems with load-controlled dynamization, and methods of installing the systems to fix a femur. The components, aspects, and features of the systems, devices, and methods described in each of these examples may be combined with one another and with the systems, devices, and methods described elsewhere herein, in any suitable combination. These examples are intended for illustration and should not limit the entire scope of the present disclosure.

Example 1. Hip Fixation System with a Nail

Figure 6:
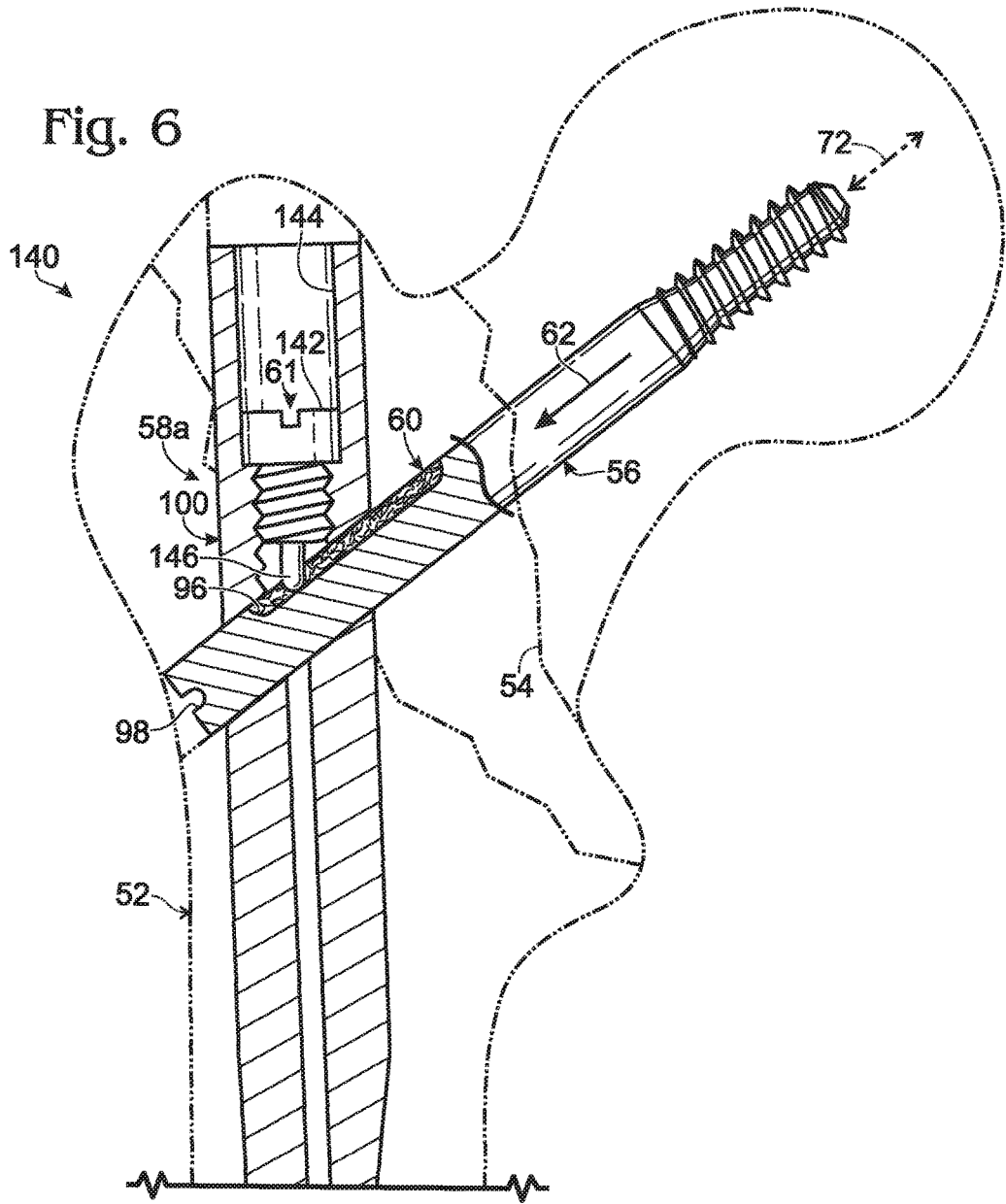
FIG. 6 is a partially sectional view of another exemplary embodiment of a hip fixation system with load-controlled dynamization, with the system attached to a fractured femur and including a support member structured as a nail and also including a fixation element extending through the nail, and with the fixation element having a deformable region configured for plastic deformation by deforming contact with a set screw inside the nail in response to a load applied to the system by a subject, in accordance with aspects of the present disclosure.

This example describes another exemplary hip fixation system 140 including a nail 100 (as a support member 58a), and a fixation element 56 attached to a deformable member 60; see FIG. 6.

Hip fixation system 140 may include any suitable combination of features described above, such as in Section I for system 50 (e.g., see FIGS. 1-5), and elsewhere in the present disclosure. However, system 140 may not utilize an outer support member 58b (compare FIGS. 1 and 6).

Fixation element 56 is pre-attached to a deformable member 60 that is positioned for contact with a stop member 61. The stop member is attached to nail and is adjustably positionable along the long axis of the nail by turning at least a portion of the stop member, to advance the stop member into an operative position that restricts rotation of the fixation element about its long axis and obstructs axial travel of the deformable member after the nail and fixation element have been placed into the femur. In the depicted embodiment, stop member 61 is structured as a set screw 142. In other embodiments, stop member 61 may be any advanceable and retractable member that attaches to the nail, such as by threaded engagement.

The deformable member may be located in a longitudinal trough 96 defined by a shaft of the fixation element and may extend any suitable distance along the trough, such as along only a portion or along the entire length of the trough (as shown here). The deformable member may be formed as a separate element that is mounted in trough 96 after formation or may be formed in the trough such as by application of a solidifiable material (e.g., a plasma spray or a polymerization solution) to the trough.

Screw 142 is received in an axial opening 144 defined by nail 100 and attaches to the nail via threaded engagement. The position of screw 142 along the long axis of the nail is adjustable by turning the screw. Screw 142 has a tip 146 configured be advanced into trough 96 after fixation element 56 has been placed into bone. Tip 146 prevents rotation of the fixation element about long axis 72. Also, the tip obstructs axial travel of deformable member 60. Contact between the tip and deformable member 60 limits and controls axial motion 62 of the fixation element and nail (including set screw 142) relative to one another. Deformation of deformable member 60 in response to load 64 allows limited axial motion 62 for compression of fracture 54. The stop member, such as screw 142, may or may not deform part of deformable member 60 as the screw is being advanced into trough 96 during system installation.

Example 2. Hip Fixation System with a Side Plate Having a Barrel Portion

Figure 7:
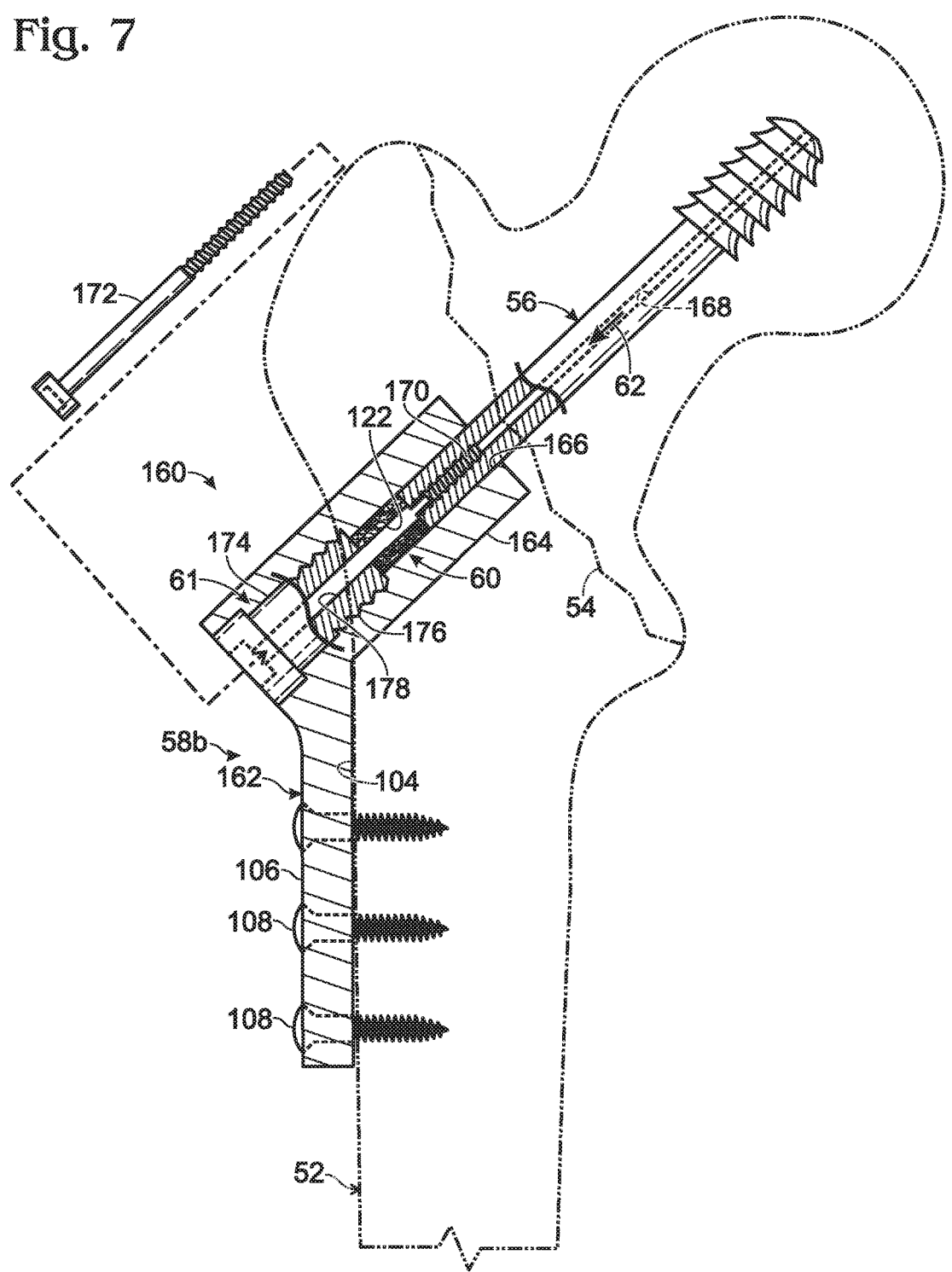
FIG. 7 is a partially sectional and exploded view of yet another exemplary embodiment of a hip fixation system with load-controlled dynamization, with the system attached to a fractured femur and including a support member structured as a side plate having a barrel portion that contains a deformable member and also including a fixation element received in the barrel portion and configured to apply a deforming force to the deformable member in cooperation with a stop member of the system, in accordance with aspects of the present disclosure.

This example describes an exemplary hip fixation system 160 including a side plate 162 (as a support member 58b) having a barrel portion 164 that extends into femur 52, and also including a deformable member 60 disposed in barrel portion 164; see FIG. 7.

Hip fixation system 160 may include any suitable combination of features described above, such as in Section I for system 50 (e.g., see FIGS. 1-5), and elsewhere in the present disclosure (e.g., Example 1). However, system 160 may not utilize an inner support member 58a (compare FIGS. 1, 6, and 7). System 160 may be suitable for fixation of an intertrochanteric fracture 54, among others.

Side plate 162 (also called a plate device) may include a mounting portion 106 from which barrel portion 164 projects. The mounting portion may be configured to be mounted on the proximal femur, such as mounted on a lateral surface region provided by lateral cortex 104. The mounting portion may define one or more openings to receive fasteners 108, such as bone screws, that attach the mounting portion to the femur. Mounting portion 106 and barrel portion 164 may be formed integrally with one another, or may be formed separately and assembled with one another before or during placement of the barrel portion into the femur and/or placement of the mounting portion onto the femur.

Barrel portion 164 is configured to be placed into the proximal femur from a lateral side thereof (e.g., after fixation element 56 is placed into the femur from the lateral side). The barrel portion defines a channel 166 in which the trailing end of fixation element 56 is received. The channel may be sized according the shaft diameter of the fixation element, to allow the fixation element to slide axially but to prevent off-axis movement of the fixation element. Alternatively, side plate 162 may be configured to permit changes to the orientation of the fixation element as described in U.S. patent application Ser. No. 14/565,105, filed Dec. 9, 2014, which is incorporated herein by reference.

Fixation element 56 may define an axial bore 168 that extends longitudinally through the fixation element. The bore allows the fixation element to be installed in the femur over a guide wire. A trailing region of the bore may include an internal thread 170 for engagement by a compression screw 172. The compression screw provides an adjustable head for the fixation element.

Barrel portion 164 also may be attached to a stop member 61. The stop member may be formed integrally with the barrel portion or may be formed separately and then attached permanently or removably to the barrel portion. In the depicted embodiment, the stop member is a removable insert 174 received in channel 166, before or after the barrel portion has been placed over the trailing end of the fixation element. Insert 174 may attach to barrel portion 164 via threaded engagement, indicated at 176, between an external thread formed by the insert and an internal thread formed inside the barrel portion by channel 166. The insert (and stop member 61 more generally) may define an axial through-hole 178 to receive the shaft of compression screw 172. The shaft of the compression screw also may extend through hole 122 of deformable member 60. A head of compression screw 172 may engage insert 174 (and stop member 61 more generally) after the compression screw has been attached to fixation element 56, to urge the fixation element toward the head of the compression screw as the compression screw is turned, to apply compression to the femur at fracture 54. The head of the compression screw may be received at least partially in a counterbore defined by through-hole 178.

A deformable member 60 may be disposed in channel 166 adjacent the trailing end of fixation element 56, and between the fixation element and stop member 61 (such as insert 174). The deformable member may be discrete and separate with respect to the stop member (such as insert 174), fixation element 56, or both. Alternatively, deformable member 60 and insert 174 (or fixation element 56) may be attached to one another before each is placed in channel 166, such that deformable member 60 and insert 174 (or fixation element 56) are installed as a unit. In any event, the insert (and stop member 61 more generally) prevents removal of deformable member 60 from the trailing end of the channel and provides a barrier for travel of the deformable member and fixation element. Furthermore, insert 174 can be manipulated (i.e., turned) to adjust the axial position of deformable member 60 along channel 166, to sandwich the deformable member between fixation element 56 and insert 174. Alternatively, system 160 may be implanted such that deformable member 60 is located between fixation element 56 and stop member 61, but is not in contact with both fixation element 56 and stop member 61 until after the system is fully implanted.

In embodiments where barrel portion 164 has an integrally formed and/or permanently attached stop member 61, deformable member 60 may be loaded into channel 166 of barrel portion 164 from the inner end thereof, before the barrel portion is placed into the femur.

Example 3. Hip Fixation Systems for Neck Fractures

This example describes exemplary hip fixation systems 180, 190 each having a deformable member 60 and configured to fix femoral neck fractures; see FIGS. 8-11.

Hip fixation systems 180, 190 may include any suitable combination of features described above, such as in Section I for system 50 (e.g., see FIGS. 1-5), and elsewhere in the present disclosure (e.g., see Example 1). However, systems 180, 190 each may (or may not) include a plurality of fixation elements 56, which may extend parallel to one another after placement into the femur. Each fixation element 56 may or may not be cannulated. Each fixation element 56 may have a head 192 that engages a lateral surface region of the femur, to block inward travel of the fixation element into the femur, such that the fixation element applies compression to the femur at fracture 54 during installation. Systems 180, 190 may include a support member 58b in the form of a buttress plate that is mounted to a lateral cortex of the femur but that does not include a barrel portion extending into the femur (compare FIG. 7 with FIGS. 8 and 9). Systems 180, 190 may not utilize an inner support member 58a (compare FIG. 1 with FIGS. 8 and 9).

Support member 58b may be attached to a plurality of stop members 61 that obstruct outward travel of deformable members 60. For example, the stop members may be formed integrally with a buttress plate or may be formed separately and then attached permanently or removably to the buttress plate.

FIG. 8 shows system 180 having a pair of deformable members 60 each positioned between an inner (bone-facing) surface of support member 58b and head 192 of the fixation element. Each deformable member 60 may (or may not) be disposed at least partially in a recess 194 defined in the inner surface of the support member.

Fixation element 56 may have a trailing extension 196 projecting outward from a flange forming head 192. Extension 196 extends through a deformable member 60 and is received in an opening 94 of support member 58b. Opening 94 may be contiguous with recess 194 and guides relative axial travel 62 of the fixation element and the support member relative to one another as each deformable member 60 is compressed.

Figure 11:
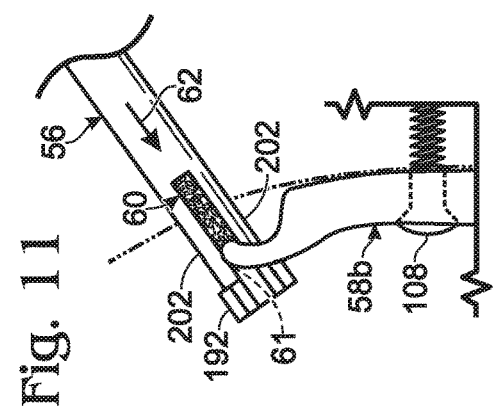
FIG. 11 is a fragmentary front view of the hip fixation system of FIG. 9, taken after deformation of the deformable member and associated axial movement of the support member and the fixation element relative to one another.
Figure 10:
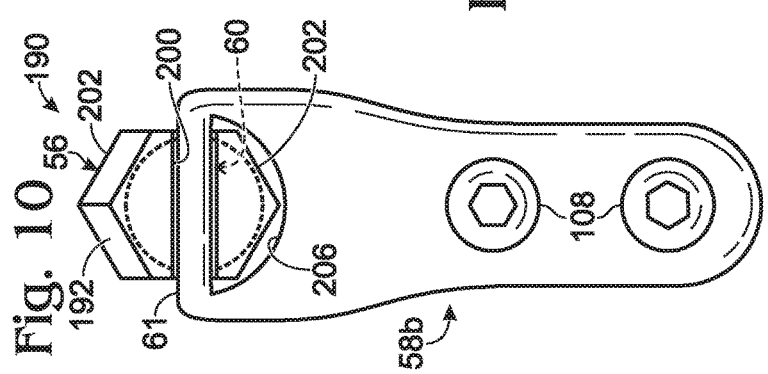
FIG. 10 is a side view of the hip fixation system of FIG. 9, taken generally along line 10-10 of FIG. 9 in the absence of the femur.

FIGS. 9-11 show system 190 having at least one fixation element 56 containing a deformable member 60 in a longitudinal slot 200 defined by the trailing portion of the fixation element. Axial bore 168 of the fixation element may extend through deformable member 60 to the trailing end of the fixation element, such that the fixation element is cannulated. Slot 200 divides a trailing portion of the fixation element into a pair of branches 202, with deformable member 60 disposed between the branches. Support member 58b may form a stop member 61 in the form of a stop bar that is received in slot 200, to engage and compress deformable member 60. The support member defines an opening 206 adjacent the stop bar to receive one of branches 202 of fixation element 56.

Example 4. Hip Fixation System with Friction-Limited Dynamization

Figure 12:
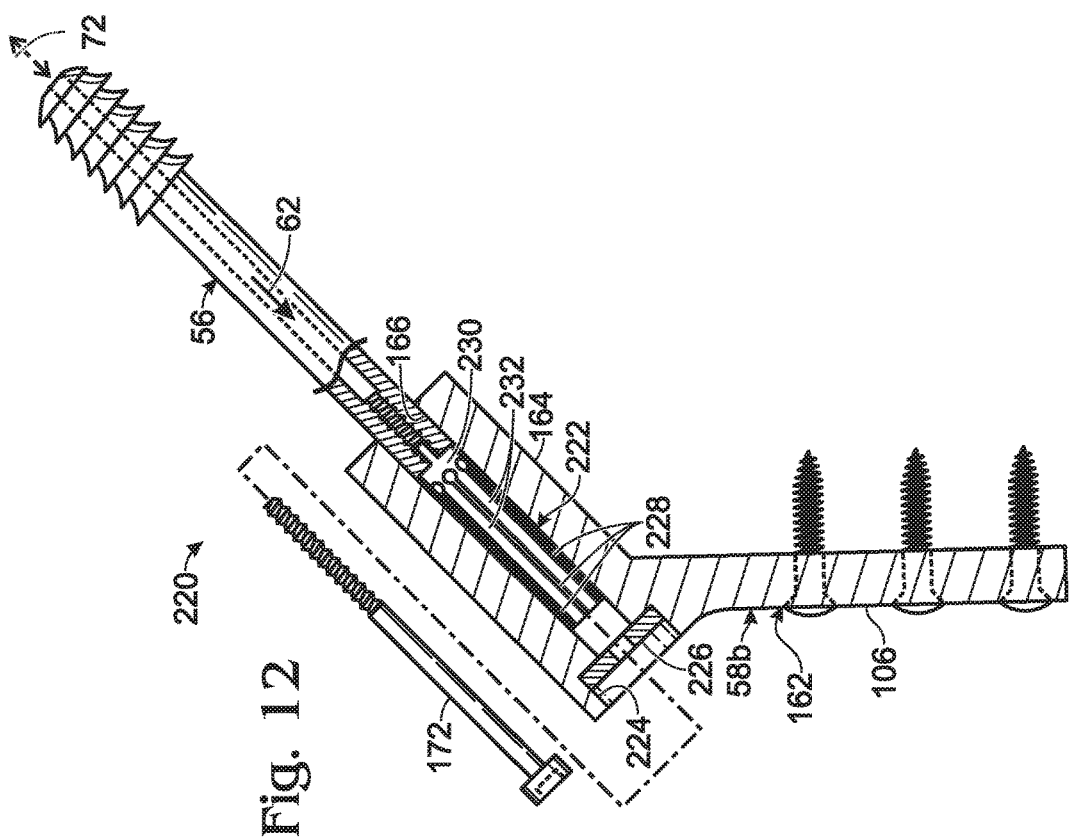
FIG. 12 is a partially sectional and exploded view of an exemplary embodiment of a hip fixation system with friction-limited dynamization, with the system including a support member in the form of a side plate having an internally tapered barrel portion, with a fixation element extending into the barrel portion and having a deformable trailing portion, and with the barrel portion providing an increasing resistance to axial travel of the side plate and the fixation element relative to one another as the barrel portion moves toward the leading end of the fixation element, in accordance with aspects of the present disclosure.

This example describes an exemplary hip fixation system 220 including a side plate 162 having a barrel portion 164 and also including a fixation element 56 that wedges into the barrel portion; see FIGS. 12 and 13.

Hip fixation system 220 may include any suitable combination of features described above, such as in Section I for system 50 (e.g., see FIGS. 1-5), and elsewhere in the present disclosure (e.g., see Example 2). However, system 220 may have a deformable region 222 that is compressible radially (toward the central long axis of the fixation element) but not compressible deformably parallel to long axis 72.

System 220 has a barrel portion 164 with a tapered channel 166 that narrows toward the outer, trailing end of the barrel portion (and toward mounting portion 106). The outer end of the channel may widen to form a counterbore 224.

System 220 has a fixation element 56 and compression screw 172 that attach to one another as described above in Example 2, to apply compression to the femur during system installation. However, insert 174 of Example 2 is replaced by a washer 226 that seats in counterbore 224 and blocks inward travel of the head of compression screw 172 toward the femoral head as compression is applied.

Fixation element 56 may define a plurality of axial slits 228 formed in the wall of the fixation element to provide communication with a central axial bore 230. The slits separate the trailing portion into a plurality of axial branches 232 each projecting away from the leading portion of the fixation element. Each axial branch 232 is deformable radially toward the central long axis of the fixation element. Radial deformation of the axial branches produces a taper in the diameter of the trailing portion of the fixation element, toward the trailing boundary thereof. Accordingly, since the inner diameter of the barrel portion also is tapered, the inside wall of the barrel portion in combination with deformable region 222 of the fixation element provide an increasing resistance to axial motion 62 of fixation element 56 and side plate 162 relative to one another, as the trailing portion of the fixation element is wedged into the barrel portion.

FIG. 13 shows barrel portion 164 with the internal taper of channel 166 more readily visible.

Example 5. Hip Fixation Systems with a Ratchet to Govern Dynamization

This example describes exemplary hip fixation systems 250, 260, and 270 each including a support member 58*b* and a fixation element 56 that collectively form a ratchet 280; see FIGS. 14-16. The ratchet provides an incrementally increasing resistance to axial travel 62 of fixation element 56 and the support member relative to one another.

Hip fixation systems 250, 260, and 270 each may include any suitable combination of features described above, such as in Section I for system 50 (e.g., see FIGS. 1-5), and elsewhere in the present disclosure (e.g., see Examples 2-4). However, system 220 may not utilize an inner support member 58*a* (compare FIGS. 1 and 14-16) and may have an elastically deformable region forming part of ratchet 280.

FIG. 14 shows system 250 including a side plate 162 having a barrel portion 164. Ratchet 280 may be formed by a series of teeth 282 defined in channel 166 by an inside wall of barrel portion 164, and at least one catch 284 (interchangeably termed a detent or pawl) defined by fixation element 56 on a shaft thereof. The catch is configured to be received in the interdental spaces (the notches) formed between teeth 282. Catch 284 may or may not be formed integrally with the shaft of the fixation element. Teeth 282 may define a diameter of channel 166 that varies along the channel to produce a series of minimum diameters alternating with a series of maximum diameters. The minimum diameters may decrease toward the trailing end of the barrel portion, such that incremental motion of catch 284 toward the outer surface of side plate 162 past each tooth 282 requires increasing force. Incremental motion of the catch in the reverse direction is selectively restricted by the asymmetrical profile of each tooth. In some embodiments, fixation element 56 may define one or more axial slits 286 that facilitate radial deformation of the fixation element near catch 284, to allow the catch to move radially inward as the catch moves between interdental spaces.

FIG. 15 shows system 260, which combines features of system 250 and system 220 (also see FIGS. 12 and 14). Ratchet 280 of system 260 is generally similar to that of system 250 except that teeth 282 are formed on the shaft of fixation element 56 and one or more catches 284 are formed by barrel portion 164 in channel 166. Fixation element 56 has slits 228 that allow radial deformation of the trailing portion of the fixation element. Catches 284 may be formed integrally with or separately from the barrel portion. The diameter of teeth 282 may decrease toward the trailing end of fixation element 56, and/or the diameter of catches 284 may decrease toward the trailing end of channel 166, such that tooth-by-tooth incremental axial motion 62 of the fixation element and side plate relative to one another requires increasing force.

FIG. 16 shows system 270 for fixation of neck fractures. The system may include one or a plurality of fixation elements 56 that each form a ratchet 280 with support member 58*b*, which is structured as a buttress plate. The ratchet is created by a series of teeth 282 arranged along a shaft of fixation element, and a catch formed by support member 58*b*. Here, catch 284 is created by an integral lip of an opening defined by the buttress plate. The lip may be movable elastically with respect to the main portion of the support member, with the aid of an elastically deformable region 290 of the support member. In other embodiments, catch 284 may be formed by a discrete component(s) with respect to the main portion of the support member.

Example 6. Selected Embodiments

This example describes selected embodiments of a hip fixation system with load-controlled dynamization and methods of hip fixation with the system.

1. A method of hip fixation with load-controlled dynamization, the method comprising: (A) stabilizing a femur with a fixation system including a femoral head fastener defining a long axis and extending from a body to a head of a femur; and (B) applying a load to the femoral head fastener via the femur to change a length of the fastener and/or an axial position of the fastener on the long axis, via an irreversible deformation of a deformable region of the fixation system.

2. The method of paragraph 1, wherein the femoral head fastener includes a movable region that moves a distance equal to the change when the load is applied, wherein the fixation system includes a fixed region arranged axially outward of the movable region and remaining fixed when the change occurs, and wherein the deformable region is disposed intermediate the movable region and the fixed region.

3. The method of paragraph 1 or paragraph 2, wherein the deformable region is provided by the femoral head fastener.

4. The method of any of paragraphs 1 to 3, wherein the step of applying a load reduces a length of the femoral head fastener.

5. The method of any of paragraphs 1 to 4, wherein the femoral head fastener includes a shaft that provides the deformable region.

6. The method of paragraph 5, wherein the shaft includes another region that is substantially resistant to deformation.

7. The method of paragraph 6, wherein the deformable region and the other region have at least substantially nonoverlapping axial extents along the femoral head fastener.

8. The method of paragraph 6, wherein the deformable region and the other region have overlapping axial extents along the femoral head fastener.

9. The method of any of paragraphs 1 to 8, wherein the femoral head fastener includes a leading element and a trailing element that are discrete from each other.

10. The method of paragraph 9, wherein the step of stabilizing a femur includes a step of adjusting a compression of a fractured region of the femur by turning the trailing element relative to the leading element.

11. The method of any of paragraphs 1 to 10, wherein the step of applying a load irreversibly deforms a region of a plate device of the fixation system via pressure exerted directly or indirectly on the region of the plate device by the femoral head fastener.

12. The method of paragraph 11, wherein the step of applying a load irreversibly deforms a discrete insert of the plate device.

13. The method of any of paragraphs 1 to 12, wherein the step of applying a load irreversibly deforms a spacer element of the fixation system disposed between the femoral head fastener and a plate device that is attached to the femur.

14. The method of any of paragraphs 1 to 13, wherein the step of stabilizing a femur arranges a nail of the fixation system longitudinally in the femur with the femoral head fastener extending transversely into and/or through the nail.

15. The method of any of paragraphs 1 to 14, wherein the step of stabilizing a femur includes a step of placing a plurality of femoral head fasteners parallel to one another.

16. The method of any of paragraphs 1 to 15, wherein the step of stabilizing a femur arranges a barrel portion of the fixation system such that the barrel portion extends into the femur, wherein the barrel portion defines a channel, and wherein the step of stabilizing a femur disposes a portion of the femoral head fastener in the channel.

17. The method of any of paragraphs 1 to 16, wherein the femoral head fastener includes a first portion and a second portion, and wherein the step of applying a load causes a region of the second portion to slide in a bore defined by the first portion to reduce a length of the femoral head fastener.

18. The method of paragraph 17, wherein an insert is disposed in the bore and is deformed irreversibly by the step of applying a load.

19. The method of any of paragraphs 1 to 18, wherein the femoral head fastener includes two or more discrete pieces that are movable relative to each other.

20. The method of paragraph 19, wherein at least a pair of the discrete pieces are disposed in threaded engagement with each other.

21. The method of any of paragraphs 1 to 20, wherein the femoral head fastener includes a spanning element that spans a fracture in the femur and also includes a compression element (such as a compression screw), and wherein the step of stabilizing includes a step of connecting the spanning element to the compression element.

22. The method of paragraph 21, wherein at least a portion of the compression element is disposed outward of the spanning element.

23. The method of any of paragraphs 1 to 22, wherein the femoral head fastener extends into one or more openings defined by a plate device, a nail, or both a plate device and a nail, after the step of stabilizing a femur.

24. The method of any of paragraphs 1 to 23, wherein the step of applying a load decreases a volume of the deformable region defined by a periphery of the deformable region.

25. The method of paragraph 24, wherein the deformable region has a cellular and/or porous structure, optionally formed of metal.

26. A method of hip fixation with load-controlled dynamization, the method comprising: stabilizing a femur with a fixation system including a femoral head fastener defining a long axis and extending from a body to a head of a femur; wherein the fixation system includes a ratchet that controls an axial position of the femoral head fastener on the long axis.

27. The method of paragraph 26, wherein the ratchet permits incremental axial travel of the femoral head fastener in an outward axial direction.

28. The method of paragraph 26 or paragraph 27, wherein the ratchet is a linear ratchet.

29. The method of any of paragraphs 26 to 28, wherein the ratchet is formed by the femoral head fastener and a wall of an opening in which the fastener is partially disposed.

30. The method of paragraph 26 or paragraph 27, wherein the ratchet is a rotary ratchet.

31. A method of hip fixation with load-controlled dynamization, the method comprising: stabilizing a femur with a fixation system including a femoral head fastener defining a long axis and extending from a body to a head of a femur; wherein the fixation system includes a barrel portion that provides an increasing resistance to outward axial travel of the femoral head fastener on the long axis by engagement of the barrel portion with the femoral head fastener.

32. The method of paragraph 31, wherein the barrel portion defines a tapered channel, further comprising a step of applying a load to the femoral head fastener via the femur to wedge the femoral fastener in the tapered channel.

33. A method of hip fixation with load-controlled dynamization, the method comprising: (A) stabilizing a femur with a fixation system including a femoral head fastener defining a long axis and extending from a body to a head of a femur; and (B) applying a load to the femoral head fastener via the femur to change an axial position of the fastener on the long axis, wherein the fixation system includes a support member disposed at least partially on the femur and having a pivotable connection to the fastener, and wherein the pivotable connection defines a pivot axis that is transverse to the long axis of the femoral head fastener.

34. The method of paragraph 33, wherein movement at the pivotable connection is governed by at least one deformable element.

35. The method of paragraph 34, wherein the at least one deformable element is elastically deformable.

36. The method of paragraph 33 or paragraph 34, wherein the pivotable connection is operatively connected to a plastically deformable member that governs a permitted pivotal range of motion at the pivotable connection.

37. A system for hip fixation with load-controlled dynamization, comprising: a femoral head fastener defining a long axis and configured to extend from a body to a head of a femur, wherein a load applied to the femoral head fastener via the femur causes an irreversible deformation of a deformable region of the fixation system and a change in a length and/or an axial position of the femoral head fastener on the long axis.

38. A system for hip fixation with load-controlled dynamization, comprising: a femoral head fastener defining a long axis and configured to extend from a body to a head of a femur; wherein the fixation system includes a ratchet that controls an axial position of the femoral head fastener on the long axis.

39. A system for hip fixation with load-controlled dynamization, comprising: a femoral head fastener defining a long axis and configured to extend from a body to a head of a femur; and a barrel portion that provides an increasing resistance to outward axial travel of the femoral head fastener on the long axis by engagement of the barrel portion with the femoral head fastener.

40. A system for hip fixation with load-controlled dynamization, comprising: a femoral head fastener defining a long axis and configured to extend from a body to a head of a femur; and a support member configured to be disposed at least partially on the femur and having a pivotable connection to the fastener, wherein the pivotable connection defines a pivot axis that is transverse to the long axis of the femoral head fastener.

41. A system for hip fixation, comprising: (A) a fixation element configured to be placed into a proximal femur of a subject such that a leading end of the fixation element is anchored in a head of the proximal femur and the fixation element extends from the head to a lateral portion of the proximal femur; and a support member configured to be connected to the proximal femur in a fixed relation to the lateral portion of the proximal femur and operatively associated with the fixation element; wherein the system includes a deformable region configured to irreversibly deform in response to a load applied to the system by the subject, such that the fixation element and the support member move relative to one another parallel to a long axis of the fixation element.

42. The system of paragraph 41, wherein the fixation element includes the deformable region, wherein the support member includes an intramedullary nail, and wherein the fixation element is configured to extend transversely through an opening defined by the intramedullary nail, further comprising a set screw received or receivable in the intramedullary nail and configured to engage the deformable region of the fixation element inside the intramedullary nail.

43. The system of paragraph 42, wherein the set screw also restricts rotation of the fixation element about the long axis.

44. The system of paragraph 42, wherein the fixation element defines an axial trough, and wherein the deformable region is formed by material located in the axial trough.

45. The system of paragraph 41, wherein the support member is configured to be mounted on a lateral cortex of the proximal femur and defines an opening to receive a region of the fixation element.

46. The system of paragraph 45, wherein the deformable region is located or locatable in the opening.

47. The system of paragraph 46, wherein the opening is a channel, and wherein the support member includes a barrel portion defining the channel and configured to be received in the proximal femur.

48. The system of paragraph 47, wherein the deformable region is provided by an insert placed into the channel of the barrel portion, and wherein the insert is discrete from the fixation element.

49. The system of system 48, further comprising a removable stop member that prevents removal of the insert from the barrel portion via an outer end of the channel.

50. The system of paragraph 49, wherein the stop member is configured to be disposed in threaded engagement with the barrel portion.

51. The system of paragraph 41, wherein the fixation element is a first fixation element, further comprising a second fixation element configured to be placed into the same proximal femur such that a leading end of the second fixation element is anchored in a head of the proximal femur and the second fixation element extends from the head to a lateral portion of the proximal femur.

52. The system of paragraph 51, wherein each fixation element has a shaft and a head fixed to one another.

53. The system of paragraph 52, where each fixation element has an extension projecting from the head of the fixation element opposite the shaft, and wherein each extension is configured to move in an opening defined by the support member when the fixation element and the support member move relative to one another parallel to a long axis of the fixation element.

54. The system of paragraph 41, wherein the fixation element is a screw having an external thread configured to anchor the screw to the head of the proximal femur.

55. The system of paragraph 41, wherein the deformable region is porous and/or cellular.

56. A method of hip fixation, the method comprising in any order: implanting a fixation system into a subject at least in part by (a) placing a fixation element into a proximal femur of the subject such that a leading end of the fixation element is anchored in a head of the proximal femur and the fixation element extends from the head to a lateral portion of the proximal femur and (b) connecting a support member to the proximal femur in a fixed relation to the lateral portion of the proximal femur; wherein the steps of (a) and (b) are performed in any order relative to one another, wherein the step of implanting operatively associates the fixation element and the support member with one another, and wherein the implanted fixation system includes a deformable region configured to irreversibly deform in response to a load applied to the system by the subject, such that the fixation element and the support member move relative to one another parallel to a long axis of the fixation element.

57. The method of paragraph 56, wherein the support member includes an intramedullary nail, and wherein the fixation element is placed into the proximal femur after the intramedullary nail is connected to the proximal femur.

58. The method of paragraph 56, wherein the step of connecting a support member includes a step of attaching a support member on a lateral cortex of the proximal femur, wherein the attached support member defines an opening, and wherein the fixation element and the deformable region are each located at least partially in the opening after the step of implanting.

59. The method of paragraph 58, wherein the opening is a channel, wherein the attached support member includes a barrel portion that defines the channel, and wherein the step of connecting a support member includes a step of inserting the barrel portion into the proximal femur.

60. The method of paragraph 56, wherein the step of placing includes a step of placing a pair of fixation elements into the head of the proximal femur, and wherein the step of implanting disposes a deformable member between the support member and each fixation element.

61. A method of hip fixation, the method comprising in any order: (A) placing a fixation element into a proximal femur of a subject such that a leading end of the fixation element is anchored in a head of the proximal femur and the fixation element extends from a lateral portion of the proximal femur to the head of the proximal femur; (B) connecting a stop member to the lateral portion of the proximal femur; and (C) operatively disposing a deformable member between the fixation element and the stop member such that the deformable member is irreversibly deformable by compressive force exerted on at least a portion of the deformable member by the fixation element and the stop member in response to a load applied to the proximal femur by the subject, such that the fixation element and the stop member move relative to one another parallel to a long axis of the fixation element.

62. A method of hip fixation, the method comprising in any order: (A) placing a nail longitudinally into a proximal femur of a subject; (B) placing a fixation element into the proximal femur such that a leading end of the fixation element is anchored in a head of the proximal femur and the fixation element extends from a lateral portion of the proximal femur, through a transverse opening of the nail, and to the head of the proximal femur, the fixation element including a shaft defining a long axis, wherein the shaft of the fixation element is attached to a deformable member before the fixation element is placed into the proximal femur; and (C) manipulating a stop member that is attached to the nail such that the stop member engages the deformable member inside the nail and restricts rotation of the fixation element about the long axis; wherein the deformable member is configured to be irreversibly deformed by compressive force exerted on at least a portion of the deformable member by the fixation element and the stop member in response to a load applied to the proximal femur by the subject, such that the fixation element and the stop member move relative to one another parallel to the long axis of the shaft.

63. A method of hip fixation, the method comprising in any order: (A) placing a fixation element into a proximal femur of a subject such that a leading end of the fixation element is anchored in a head of the proximal femur and the fixation element extends from a lateral portion of the proximal femur and to the head of the proximal femur; (B) attaching a side plate to a lateral cortex of the proximal femur, the side plate including a barrel portion that defines a channel that extends into the proximal femur and receives a trailing portion of the fixation element; (C) attaching a stop member to the barrel portion; and (D) disposing a deformable member in the channel between the trailing portion of the fixation element and the stop member, wherein the deformable member is configured to be irreversibly deformed in response to a load applied to the system by the subject, such that the fixation element and the barrel portion move relative to one another parallel to the long axis.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

I claim:

1. A method of hip fixation, the method comprising in any order:
    placing a fixation element into a proximal femur of a subject, such that a leading end of the fixation element is anchored in a head of the proximal femur and such that the fixation element extends from a lateral portion of the proximal femur to the head of the proximal femur;
    connecting a stop member to the proximal femur; and
    operatively disposing a deformable member, such that the deformable member is configured to be plastically deformed by compressive force exerted on at least a portion of the deformable member by the fixation element and the stop member in response to a load applied to the proximal femur by the subject, wherein plastic deformation of the deformable member is accompanied by movement of at least the leading end of the fixation element and the stop member relative to one another parallel to a long axis of the fixation element.

2. The method of claim 1, wherein the step of placing a fixation element includes a step of placing a fixation element as a unit into the proximal femur, and wherein plastic deformation of the deformable member is accompanied by movement of the entire fixation element and the stop member relative to one another parallel to the long axis of the fixation element.

3. The method of claim 1, further comprising a step of disposing a nail in the proximal femur, wherein the nail defines a transverse opening, and wherein the step of placing a fixation element includes a step of placing a portion of the fixation element through the transverse opening after the step of disposing a nail.

4. The method of claim 3, wherein the nail and the stop member are placed into the proximal femur as a unit.

5. The method of claim 3, wherein the step of operatively disposing a deformable member includes a step of adjusting a position of the stop member with respect to the nail and the fixation element after the step of connecting a stop member to the proximal femur.

6. The method of claim 1, further comprising a step of attaching a plate device to a lateral cortex of the proximal femur, and a step of placing a barrel portion of the plate device into the proximal femur, wherein a portion of the fixation element is disposed in the barrel portion after completion of the steps of attaching a plate device and placing a fixation element.

7. The method of claim 6, wherein the step of connecting a stop member includes a step of connecting a stop member to the proximal femur via the plate device.

8. The method of claim 7, wherein at least a portion of the stop member is disposed in the barrel portion of the plate device after completion of the step of operatively disposing a deformable member.

9. The method of claim 1, wherein the step of placing a fixation element includes a step of placing a plurality of fixation elements into the proximal femur parallel to one another, and wherein the step of operatively disposing a deformable member includes a step of operatively disposing a deformable member between each fixation element and a stop member.

10. A method of hip fixation, the method comprising:
stabilizing a proximal femur of a subject by implanting a fixation system including a fixation element defining a long axis and extending from a lateral portion of the proximal femur to a head of the proximal femur, the fixation system including a selectively deformable member and a stop member;
wherein the implanted fixation system is configured such that the subject applies a load to the fixation element via the proximal femur to change a position of at least a portion of the fixation element with respect to the stop member by movement of the at least a portion of the fixation element and the stop member relative to one another parallel to the long axis as the deformable member deforms plastically.

11. The method of claim 10, wherein the deformable member is provided by the fixation element.

12. The method of claim 11, wherein the fixation element includes a leading element and a trailing element that are discrete from each other and configured to move relative to one another as the deformable member deforms plastically.

13. The method of claim 10, wherein the step of stabilizing a proximal femur includes a step of attaching a plate device to the lateral portion of the proximal femur, and wherein the deformable member is provided or held by the plate device.

14. The method of claim 10, wherein the step of stabilizing a proximal femur includes a step of operatively disposing the deformable member between the fixation element and the stop member, and wherein the fixation element and the stop member are configured to apply compressive force to the deformable member in response to the load.

15. The method of claim 10, wherein the step of stabilizing a proximal femur includes a step of arranging a nail of the fixation system longitudinally in the proximal femur, and a step of placing a portion of the fixation element through a transverse opening of the nail.

16. A method of hip fixation, the method comprising:
implanting a fixation system into a subject at least in part by (a) placing a fixation element into a proximal femur of the subject, such that a leading end of the fixation element is anchored in a head of the proximal femur and such that the fixation element extends from a lateral portion of the proximal femur to the head of the proximal femur, and (b) connecting a plate device or a nail to the proximal femur in a fixed relation to the lateral portion of the proximal femur;
wherein steps (a) and (b) are performed in any order relative to one another,
wherein the step of implanting operatively associates the fixation element and the plate device or the nail with one another, and
wherein the implanted fixation system includes a deformable member configured to plastically deform in response to a load applied to the fixation element by the proximal femur of the subject, such that the fixation element and the plate device or the nail move relative to one another parallel to a long axis of the fixation element.

17. The method of claim 16, wherein fixation system includes a nail, and wherein the fixation element extends transversely through the nail after the step of implanting.

18. The method of claim 16, wherein the step of connecting a plate device or a nail includes a step of attaching a plate device on a lateral cortex of the proximal femur, wherein the plate device defines an opening, and wherein the fixation element and the deformable member are each located at least partially in the opening after the step of implanting.

19. The method of claim 18, wherein the plate device includes a barrel portion, and wherein the step of connecting a plate device or a nail includes a step of inserting the barrel portion into the proximal femur.

20. The method of claim 16, wherein the step of placing a fixation element includes a step of placing a pair of fixation elements into the head of the proximal femur, and wherein the step of implanting operatively disposes a deformable member between a plate device and each fixation element.

* * * * *